US006180367B1

(12) United States Patent
Leung et al.

(10) Patent No.: US 6,180,367 B1
(45) Date of Patent: Jan. 30, 2001

(54) PROCESS FOR BACTERIAL PRODUCTION OF POLYPEPTIDES

(75) Inventors: Woon-Lam Susan Leung, San Mateo; James R. Swartz, Menlo Park, both of CA (US)

(73) Assignee: Genentech, Inc., South San Francisco, CA (US)

(*) Notice: Under 35 U.S.C. 154(b), the term of this patent shall be extended for 0 days.

(21) Appl. No.: 09/422,712

(22) Filed: Oct. 21, 1999

Related U.S. Application Data

(60) Provisional application No. 60/106,052, filed on Oct. 28, 1998.

(51) Int. Cl.[7] ..................................................... C12P 21/00

(52) U.S. Cl. .................... 435/69.1; 435/69.7; 435/252.1; 435/252.3

(58) Field of Search ............................... 435/69.1, 320.1, 435/252.1, 252.3, 252.33, 69.7; 536/23.1

(56) References Cited

U.S. PATENT DOCUMENTS

| | | |
|---|---|---|
| 4,595,658 | 6/1986 | Zinder et al. . |
| 4,637,980 | 1/1987 | Auerbach et al. . |
| 5,169,772 | 12/1992 | Zimmerman et al. . |

FOREIGN PATENT DOCUMENTS

| | | |
|---|---|---|
| 155189 | 9/1985 | (EP) . |
| 61-257931 | 11/1986 | (JP) . |
| 2043415 | 9/1995 | (RU) . |
| 2071501 | 1/1997 | (RU) . |
| 2071503 | 1/1997 | (RU) . |
| WO 87/02702 | 5/1987 | (WO) . |
| WO 93/24633 | 12/1993 | (WO) . |
| WO 94/12214 | 6/1994 | (WO) . |

OTHER PUBLICATIONS

Ames et al., "Simple, rapid, and quantitative release of periplasmic proteins by chloroform" *Journal of Bacteriology* 160(3):1181–1183 (Dec. 1984).

Ariga et al., "Release of thermophilic α–amylase from transformed *Escherichia coli* by addition of glycine" *Journal of Fermentation and Bioengineering* 68(4):243–246 (1989).

Asami et al., "Synchronized disruption of *Escherichia coli* cells by T4 phage infection" *Journal of Fermentation and Bioengineering* 83(6):511–516 (1997).

(List continued on next page.)

*Primary Examiner*—David Guzo
*Assistant Examiner*—Gerald George Leffers, Jr.
(74) *Attorney, Agent, or Firm*—Janet E. Hasak

(57) ABSTRACT

Processes are described for recovering heterologous polypeptide from bacterial cells, including the periplasm and cytoplasm. One process involves culturing the bacterial cells, which cells comprise nucleic acid encoding phage lysozyme and nucleic acid encoding a protein that displays DNA-digesting activity, wherein these nucleic acids are linked to a first promoter, and nucleic acid encoding the heterologous polypeptide, which nucleic acid is linked to a second promoter, under certain conditions to produce a broth lysate; and recovering accumulated heterologous polypeptide from the broth lysate. Another process entails culturing bacterial cells that comprise nucleic acid encoding phage lysozyme, gene t, and nucleic acid encoding a protein that displays DNA-digesting activity under the control of a signal sequence for secretion of said DNA-digesting protein, wherein said nucleic acids are linked to one or more promoters, and nucleic acid encoding the heterologous polypeptide and a signal sequence for secretion of the heterologous polypeptide, which nucleic acid encoding the heterologous polypeptide is linked to a another promoter that is inducible, under certain conditions to produce a broth lysate; and recovering accumulated heterologous polypeptide from the broth lysate.

12 Claims, 13 Drawing Sheets

OTHER PUBLICATIONS

Carter et al., "High level *Escherichia coli* expression and production of a bivalent humanized antibody fragment" *Bio–Technology* 10:163–167 (1992).

Dabora and Cooney, "Intracellular lytic enzyme systems and their use for disruption of *Escherichia coli*" *Advances in Biochemical Engineering/Biotechnology*, A. Fiechter, ed., Berlin:Springer–Verlag vol. 43:11–30 (1990).

French et al., "Development of a simple method for the recovery of recombinant proteins from the *Escherichia coli* periplasm" *Enzyme and Microbial Technology* 19:332–338 (1996).

Hart et al., "Large Scale, In Situ Isolation of Periplasmic IGF–I from *E. coli*" *Bio/Technology* 12:1113–1117 (Nov. 1994).

Hobot et al., "Periplasmic gel: new concept resulting from the reinvestigation of bacterial cell envelope ultrastructure by new methods" *Journal of Bacteriology* 160(1):143–152 (Oct. 1984).

"Isolation and purification of cell walls" *Bacterial Cell Surface Techniques*, Hancock and Poxton eds., New York:John Wiley & Sons Ltd., Chapter 3, pp. 55–65 (1988).

Jekel and Wackernagel, "The periplasmic endonuclease I of *Escherichia coli* has amino–acid sequence homology to the extracellular DNases of Vibrio cholerae and Aeromonas hydrophila" *Gene* 154(1):55–59 (Feb. 27, 1995).

Joseph–Liauzun et al., "Human recombinant interleukin–1β isolated from *Escherichia coli* by simple osmotic shock" *Gene* 86(2):291–295 (Feb. 14, 1990).

Josslin, R., "The lysis mechanism of phage T4: mutants affecting lysis" *Virology* 40(3):719–726 (Mar. 1970).

"Lysozyme" *Worthington Enzyme Manual*, Worthington, C. ed., New Jersey:Worthington Biochemical Corporation pp. 219–223 (1988).

Matthews et al., "Relation between hen egg white lysozyme and bacteriophage T4 lysozyme: evolutionary implications" *Journal of Molecular Biology* 147(4):545–558 (Apr. 25, 1981).

Mukai et al., "The mechanism of lysis in phage T4–infected cells" *Virology* 33(3):398–404 (Nov. 1967).

Naglak and Wang, "Recovery of a foreign protein from the periplasm of *Escherichia coli* by chemical permeabilization" *Enzyme & Microbial Technology* 12(8):603–611 (Aug. 1990).

Neu and Heppel, "The release of enzymes from *Escherichia coli* by osmotic shock and during the formation of spheroplasts" *Journal of Biological Chemistry* 240(9):3685–3692 (Sep. 1965).

Neu and Heppel, "The release of ribonuclease into the medium when *Escherichia coli* cells are converted to spherosplasts" *Journal of Biological Chemistry* 239(11):3893–3900 (Nov. 1964).

Nossal and Heppel, "The release of enzymes by osmotic shock from *Escherichia coli* in exponential phase" *Journal of Biological Chemistry* 241(13):3055–3062 (Jul. 10, 1966).

Pierce et al., "Expression and recovery of recombinant periplasmically secreted α amylase derived from streptomyces thermoviolaceus" *The 1995 ICheme Research Event/First Eurpoean Conference* 2:995–997 (1995).

Pugsley and Schwartz, "Export and secretion of proteins by bacteria" *FEMS (Federation of European Microbiological Societies) Microbiology Reviews* 32:3–38 (1985).

Stabel et al., "Periplasmic location of *Brucella abortus* Cu/Zn superoxide dismutase" *Veterinary Microbiology* 38(4):307–314 (Feb. 1994).

Swartz et al., "*E. coli* host modifications for improved rDNA product quality and product recovery" (Abstract orally presented at the Separation Technology VII meeting entitled " Separations for Clean Production" sponsored by the Engineering Foundation held in Davos, Switzerland on Oct. 28, 1997).

Tanji et al., "Controlled expression of lysis genes encoded inT4 phage for the gentle disruption of *Escherichia coli* cells" *Journal of Fermentation and Bioengineering* 85(1):74–78 (1998).

Tsugita and Inouye, "Complete primary structure of phage lysozyme from *Escherichia coli* T4" *Journal of Molecular Biology* 37(1):201–212 (Oct. 14, 1968).

Tsugita and Inouye, "Purification of bacteriophage T4 lysozyme" *Journal of Biological Chemistry* 243(2):391–397 (Jan. 25, 1968).

Witholt et al., "How does lysozyme penetrate through the bacterial outer membrane?" *Biochimica et Biophysica Acta* 44(3):534–544 (Sep. 7, 1976).

Zinder and Arndt, "Production of protoplasts of *Escherichia coli* by lysozyme treatment" *Proc. Natl. Acad. Sci. USA* 42:586–590 (1956).

Leung et al., "Genetic manipulations to improved large–scale product recovery" *Abstract Papers of the American Chemical Society* 216 Meeting (Pt. 1):Biot014 (1998).

Lin, J., "Endonuclease A degrades chromosomal and plasmid DNA of *Escherichia coli* present in most preparations of single stranded DNA from phagemids" *Proceedings of the National Science Council, Republic of China—Part B, Life Sciences* 16(1):1–5 (Jan. 1992).

Lu and Henning, "Lysis protein T of bacteriophage T4" *Molecular and General Genetics* 235(2–3):253–258 (Nov. 1992).

*Molecular Biology of Bacteriophage T4* (American Society for Microbiology), J.D. Karam, ed. in chief, Washington DC:ASM Press pp. 398–399 (1994).

Souther et al., "Degradation of *Escherichia coli* chromosome after infection by bacteriophage T4: role of bacteriophage gene D2a" *Journal of Virology* 10(5):979–984 (Nov. 1972).

Wan and Baneyx, "TolAIII co–overexpression facilitates the recovery of periplasmic recombinant proteins into the growth medium of *Escherichia coli*" *Protein Expression & Purification* 14(1):13–22 (Oct. 1998).

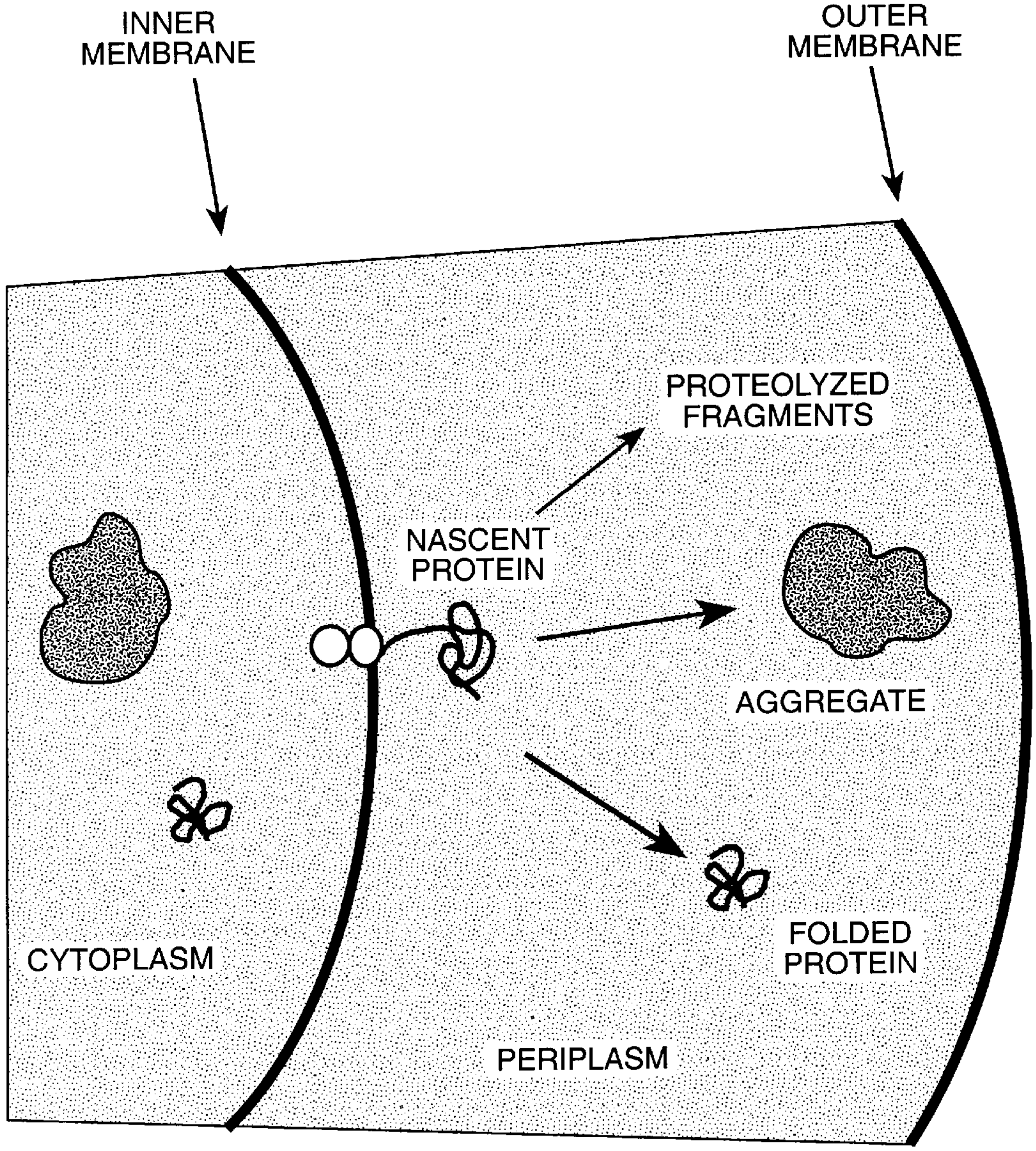
FIG._1

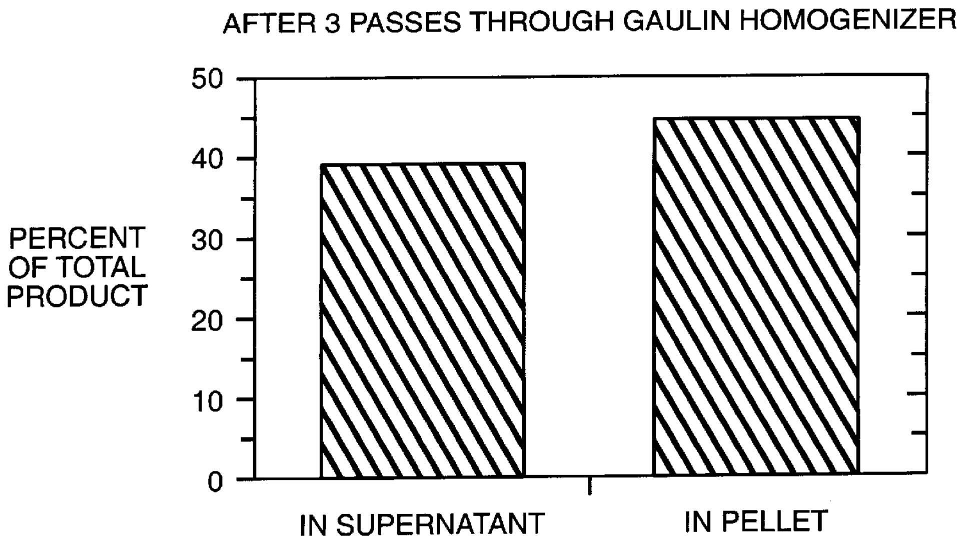
FIG._2
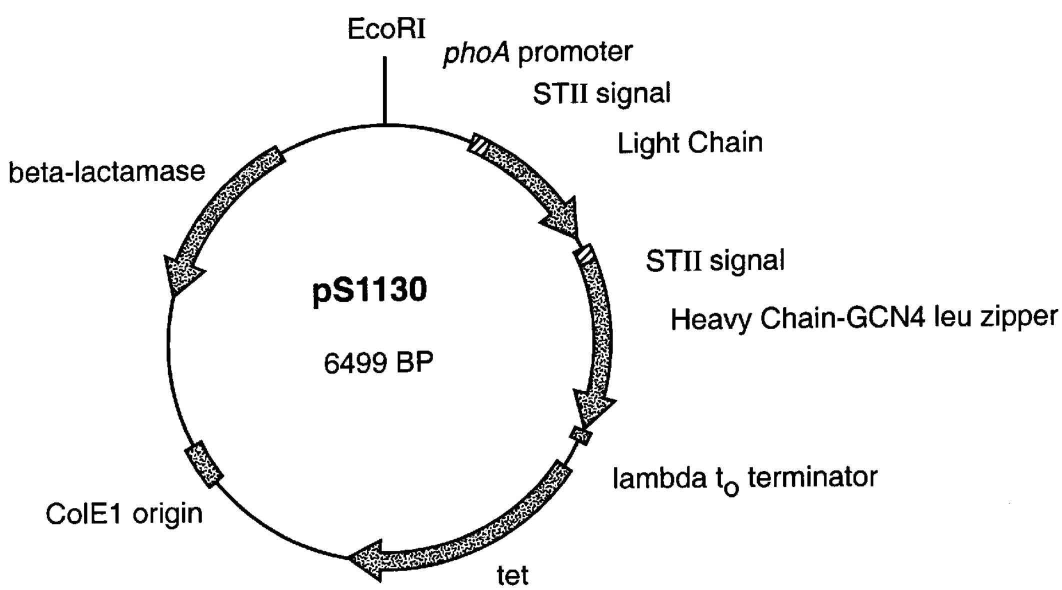
FIG._3

Start of expression cassette

```
  1 GAATTCAACT TCTCCATACT TTGGATAAGG AAATACAGAC ATGAAAAATC TCATTGCTGA

 61 GTTGTTATTT AAGCTTTGGA GATTATCGTC ACTGCAATGC TTCGCAATAT GGCGCAAAAT

121 GACCAACAGC GGTTGATTGA TCAGGTAGAG GGGGCGCTGT ACGAGGTAAA GCCCGATGCC

181 AGCATTCCTG ACGACGATAC GGAGCTGCTG CGCGATTACG TAAAGAAGTT ATTGAAGCAT

241 CCTCGTCAGT AAAAAGTTAA TCTTTTCAAC AGCTGTCATA AAGTTGTCAC GGCCGAGACT

301 TATAGTCGCT TTGTTTTTAT TTTTTAATGT ATTTGTAACT AGAATTCGAG CTCGCCGGGG

361 ATCCTCTAGA GGTTGAGGTG ATTTT ATG AAA AAG AAT ATC GCA TTT CTT CTT
-23                            M   K   K   N   I   A   F   L   L

413 GCA TCT ATG TTC GTT TTT TCT ATT GCT ACA AAC GCG TAC GCT GAT ATC
-14 A   S   M   F   V   F   S   I   A   T   N   A   Y   A   D   I

461 CAG ATG ACC CAG TCC CCG AGC TCC CTG TCC GCC TCT GTG GGC GAT AGG
  3 Q   M   T   Q   S   P   S   S   L   S   A   S   V   G   D   R

509 GTC ACC ATC ACC TGT CGT GCC AGT CAG GAC ATC AAC AAT TAT CTG AAC
 19 V   T   I   T   C   R   A   S   Q   D   I   N   N   Y   L   N

557 TGG TAT CAA CAG AAA CCA GGA AAA GCT CCG AAA CTA CTG ATT TAC TAT
 35 W   Y   Q   Q   K   P   G   K   A   P   K   L   L   I   Y   Y

605 ACC TCC ACC CTC CAC TCT GGA GTC CCT TCT CGC TTC TCT GGT TCT GGT
 51 T   S   T   L   H   S   G   V   P   S   R   F   S   G   S   G
```

FIG._4A-1

```
653 TCT GGG ACG GAT TAC ACT CTG ACC ATC AGC AGT CTG CAA CCG GAG GAC
 67 S   G   T   D   Y   T   L   T   I   S   S   L   Q   P   E   D

701 TTC GCA ACT TAT TAC TGT CAG CAA GGT AAT ACT CTG CCG CCG ACG TTC
 83 F   A   T   Y   Y   C   Q   Q   G   N   T   L   P   P   T   F

749 GGA CAG GGC ACG AAG GTG GAG ATC AAA CGA ACT GTG GCT GCA CCA TCT
 99 G   Q   G   T   K   V   E   I   K   R   T   V   A   A   P   S

797 GTC TTC ATC TTC CCG CCA TCT GAT GAG CAG TTG AAA TCT GGA ACT GCC
115 V   F   I   F   P   P   S   D   E   Q   L   K   S   G   T   A

845 TCT GTT GTG TGC CTG CTG AAT AAC TTC TAT CCC AGA GAG GCC AAA GTA
131 S   V   V   C   L   L   N   N   F   Y   P   R   E   A   K   V

893 CAG TGG AAG GTG GAT AAC GCC CTC CAA TCG GGT AAC TCC CAG GAG AGT
147 Q   W   K   V   D   N   A   L   Q   S   G   N   S   Q   E   S

941 GTC ACA GAG CAG GAC AGC AAG GAC AGC ACC TAC AGC CTC AGC AGC ACC
163 V   T   E   Q   D   S   K   D   S   T   Y   S   L   S   S   T

989 CTG ACG CTG AGC AAA GCA GAC TAC GAG AAA CAC AAA GTC TAC GCC TGC
179 L   T   L   S   K   A   D   Y   E   K   H   K   V   Y   A   C

1037 GAA GTC ACC CAT CAG GGC CTG AGC TCG CCC GTC ACA AAG AGC TTC AAC
 195 E   V   T   H   Q   G   L   S   S   P   V   T   K   S   F   N

1085 AGG GGA GAG TGT TAA  G CTGATCCTCT ACGCCGGACG CATCGTGGCG
 211 R   G   E   C
```

FIG._4A-2

```
1131 CTAGTACGCA AGTTCACGTA AAAACGGTAT CTAGAGGTTG AGGTGATTTT  ATG AAA
 -23                                                        M   K

1187 AAG AAT ATC GCA TTT CTT CTT GCA TCT ATG TTC GTT TTT TCT ATT GCT
 -21 K   N   I   A   F   L   L   A   S   M   F   V   F   S   I   A

1235 ACA AAC GCG TAC GCT GAG GTT CAG CTG GTG GAG TCT GGC GGT GGC CTG
  -5 T   N   A   Y   A   E   V   Q   L   V   E   S   G   G   G   L

1283 GTG CAG CCA GGG GGC TCA CTC CGT TTG TCC TGT GCA ACT TCT GGC TAC
  12 V   Q   P   G   G   S   L   R   L   S   C   A   T   S   G   Y

1331 ACC TTT ACC GAA TAC ACT ATG CAC TGG ATG CGT CAG GCC CCG GGT AAG
  28 T   F   T   E   Y   T   M   H   W   M   R   Q   A   P   G   K

1379 GGC CTG GAA TGG GTT GCA GGG ATT AAT CCT AAA AAC GGT GGT ACC AGC
  44 G   L   E   W   V   A   G   I   N   P   K   N   G   G   T   S

1427 CAC AAC CAG AGG TTC ATG GAC CGT TTC ACT ATA AGC GTA GAT AAA TCC
  60 H   N   Q   R   F   M   D   R   F   T   I   S   V   D   K   S

1475 ACC AGT ACA GCC TAC ATG CAA ATG AAC AGC CTG CGT GCT GAG GAC ACT
  76 T   S   T   A   Y   M   Q   M   N   S   L   R   A   E   D   T

1523 GCC GTC TAT TAT TGT GCT AGA TGG CGA GGC CTG AAC TAC GGC TTT GAC
  92 A   V   Y   Y   C   A   R   W   R   G   L   N   Y   G   F   D

1571 GTC CGT TAT TTT GAC GTC TGG GGT CAA GGA ACC CTG GTC ACC GTC TCC
 108 V   R   Y   F   D   V   W   G   Q   G   T   L   V   T   V   S

1619 TCG GCC TCC ACC AAG GGC CCA TCG GTC TTC CCC CTG GCA CCC TCC TCC
 124 S   A   S   T   K   G   P   S   V   F   P   L   A   P   S   S
```

FIG._4B-1

1667 AAG AGC ACC TCT GGG GGC ACA GCG GCC CTG GGC TGC CTG GTC AAG GAC
140 K S T S G G T A A L G C L V K D

1715 TAC TTC CCC GAA CCG GTG ACG GTG TCG TGG AAC TCA GGC GCC CTG ACC
156 Y F P E P V T V S W N S G A L T

1763 AGC GGC GTG CAC ACC TTC CCG GCT GTC CTA CAG TCC TCA GGA CTC TAC
172 S G V H T F P A V L Q S S G L Y

1811 TCC CTC AGC AGC GTG GTG ACC GTG CCC TCC AGC AGC TTG GGC ACC CAG
188 S L S S V V T V P S S S L G T Q

1859 ACC TAC ATC TGC AAC GTG AAT CAC AAG CCC AGC AAC ACC AAG GTC GAC
204 T Y I C N V N H K P S N T K V D

1907 AAG AAA GTT GAG CCC AAA TCT TGT GAC AAA ACT CAC ACA TGC CCG CCG
220 K K V E P K S C D K T H T C P P

1955 TGC CCA GCA CCA GAA CTG CTG GGC GGC CGC ATG AAA CAG CTA GAG GAC
236 C P A P E L L G G R M K Q L E D

2003 AAG GTC GAA GAG CTA CTC TCC AAG AAC TAC CAC CTA GAG AAT GAA GTG
252 K V E E L L S K N Y H L E N E V

2051 GCA AGA CTC AAA AAG CTT GTC GGG GAG CGC TAA GCATGCG ACGGCCCTAG
268 A R L K K L V G E R

2101 AGTCCCTAAC GCTCGGTTGC CGCCGGGCGT TTTTTATTGT TAA

FIG._4B-2

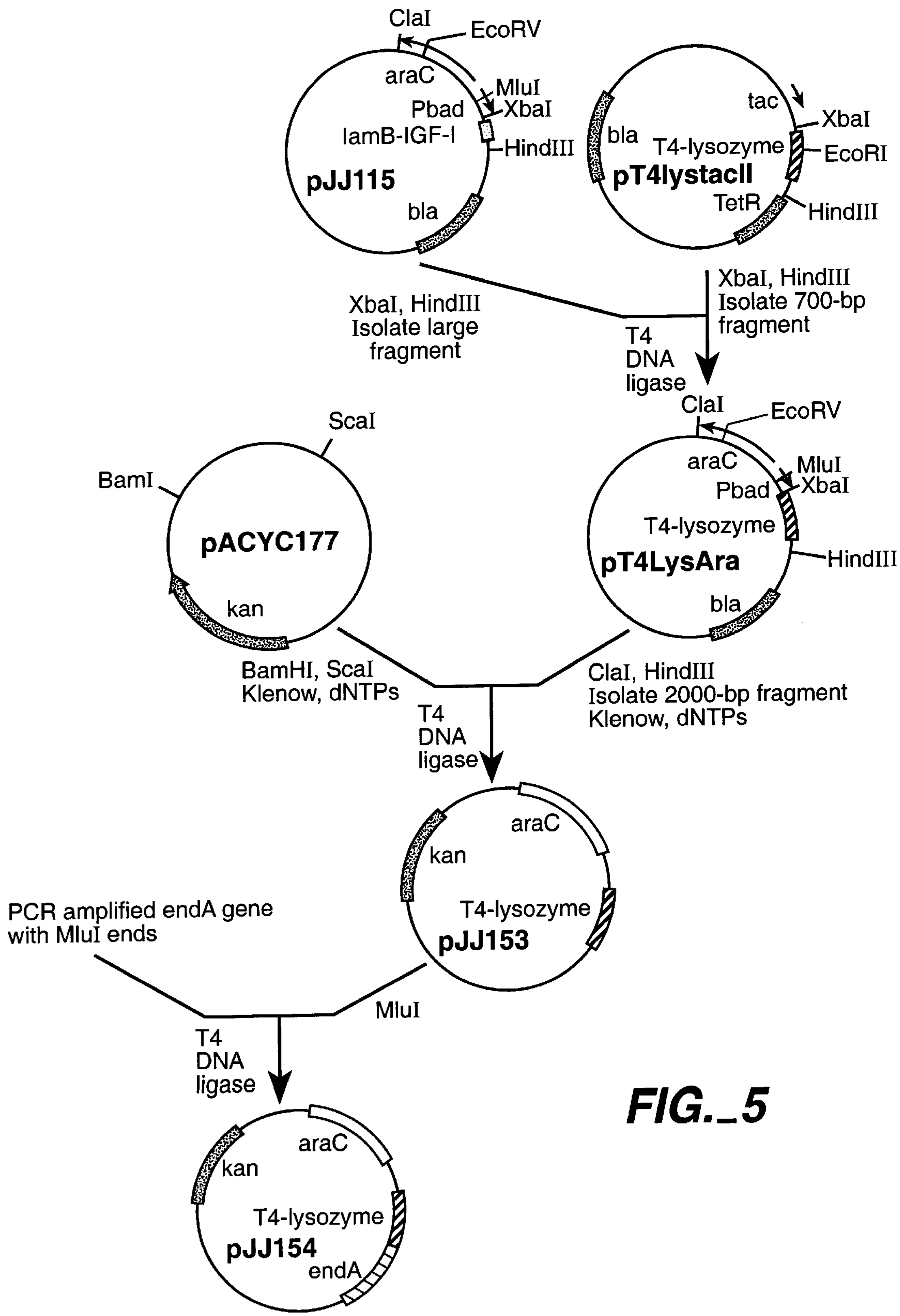
FIG._5

FIG._6
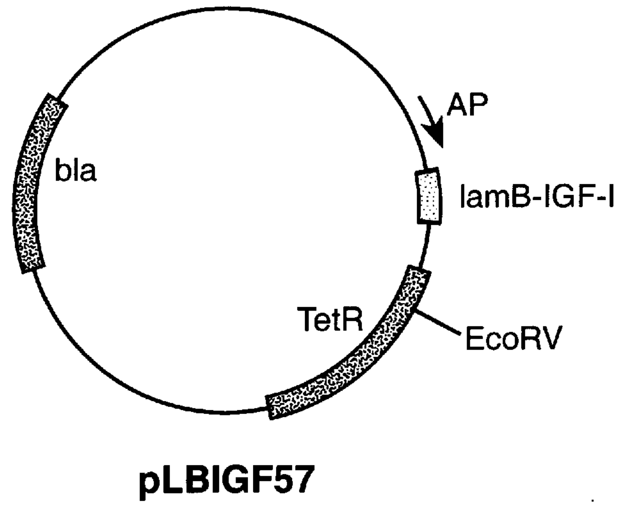
FIG._7
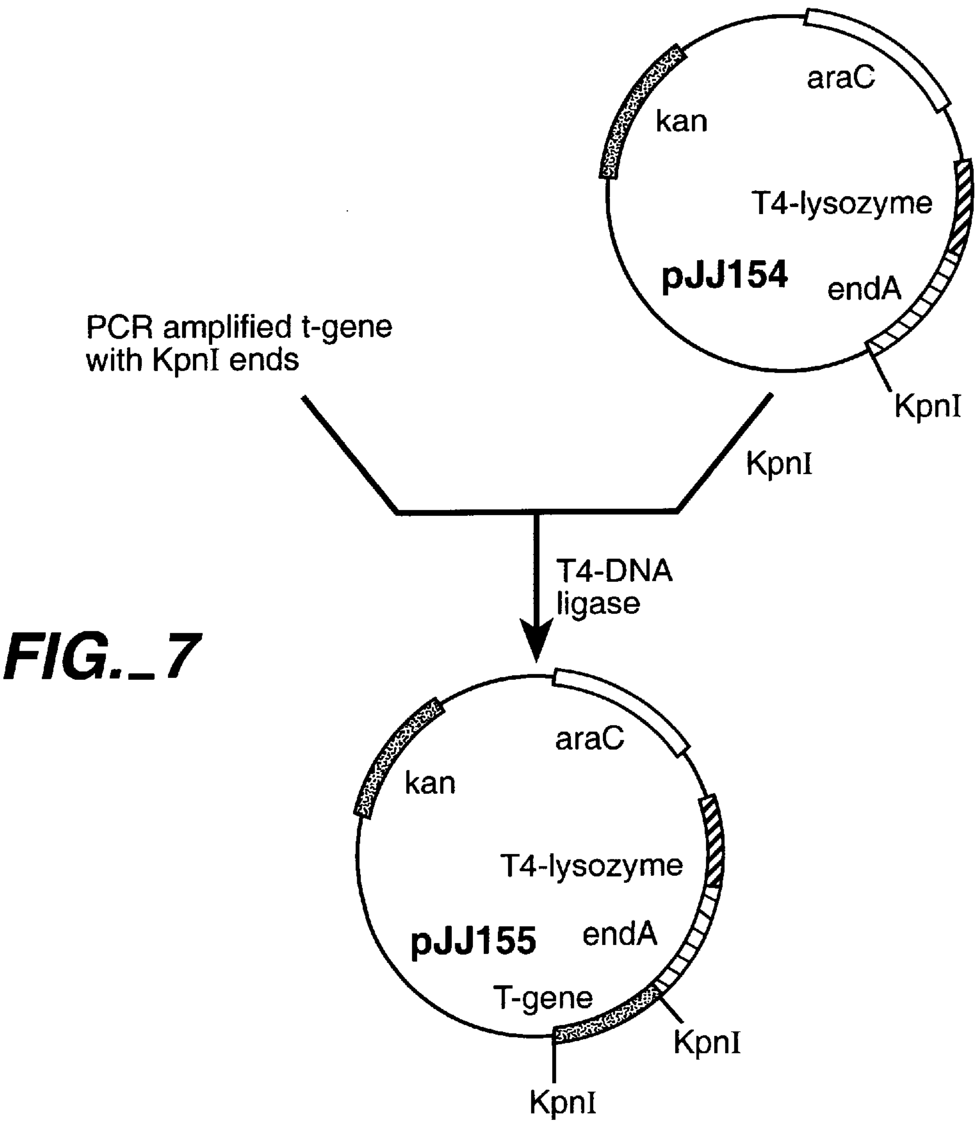

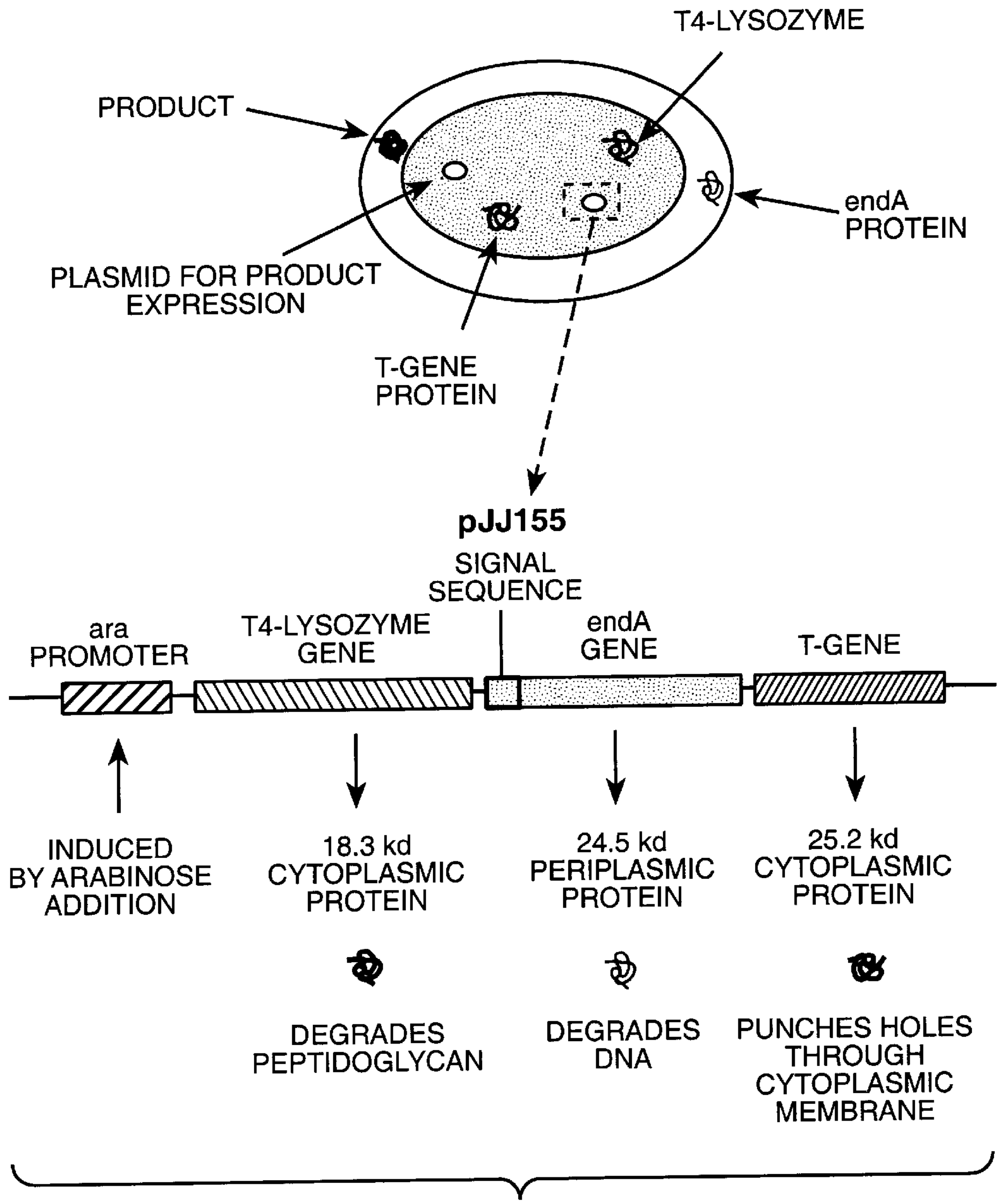
FIG._8

CONTROL BROTH BEFORE EDTA ADDITION
RESUSPENDED PELLET
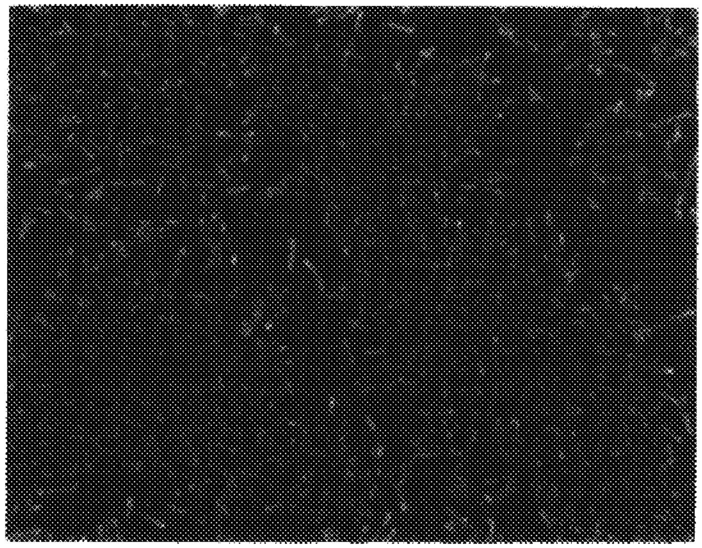
FIG._9A
CONTROL BROTH AFTER EDTA ADDITION
RESUSPENDED PELLET
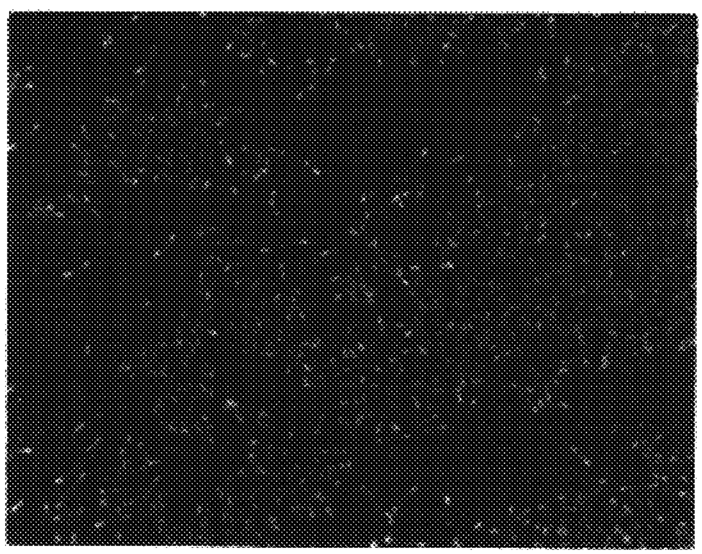
FIG._9B BROTH WITH T4-LYSOZYME +endA +t-GENE CO-EXPRESSION FERMENTATION HARVEST WHOLE BROTH - UNDILUTED WHOLE BROTH
FIG._9C
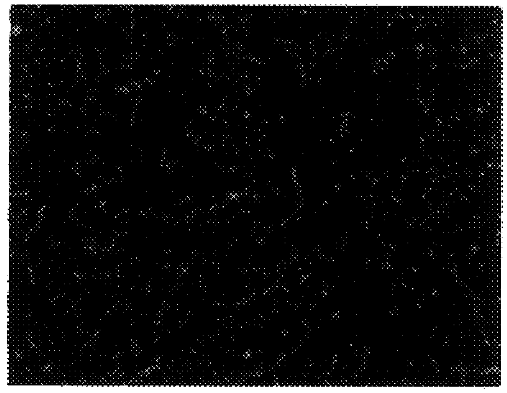
BROTH WITH T4-LYSOZYME +endA +t-GENE CO-EXPRESSION BEFORE EDTA ADDITION - RESUSPENDED PELLET
FIG._9D
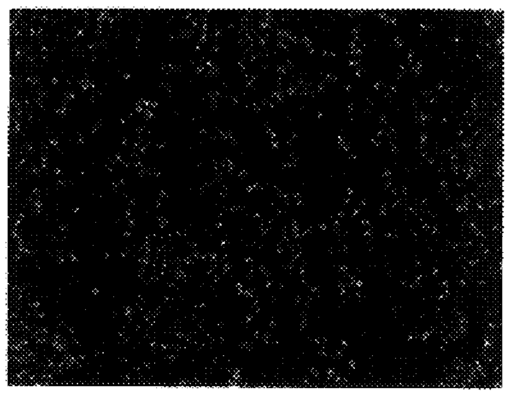
BROTH WITH T4-LYSOZYME +endA +t-GENE CO-EXPRESSION AFTER EDTA ADDITION - RESUSPENDED PELLET
FIG._9E
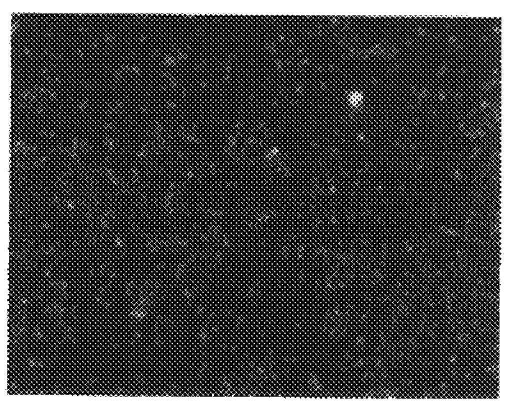

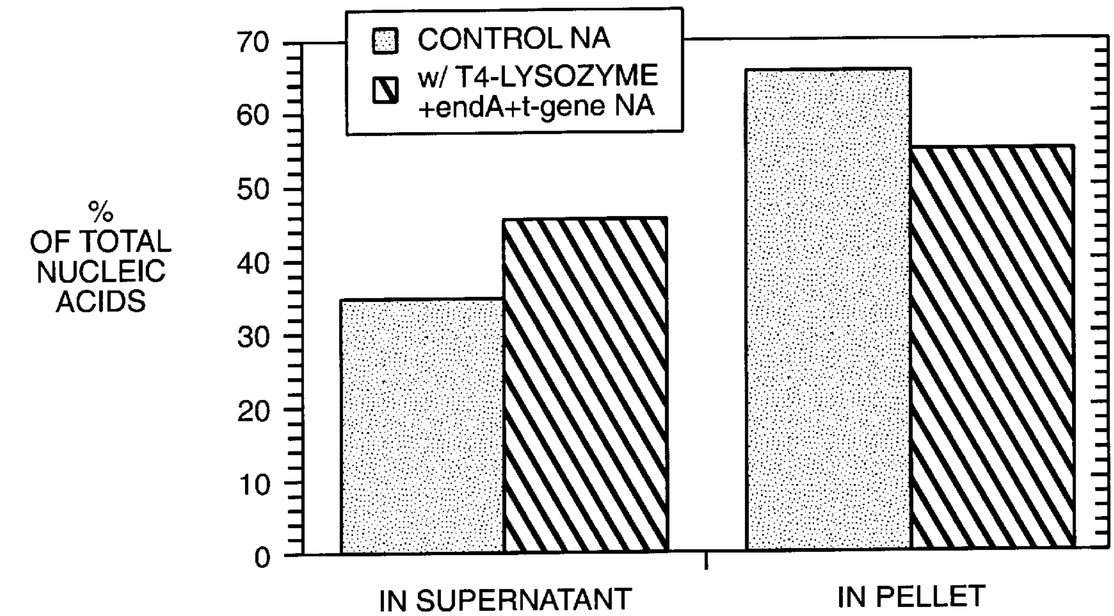
*FIG._10A*
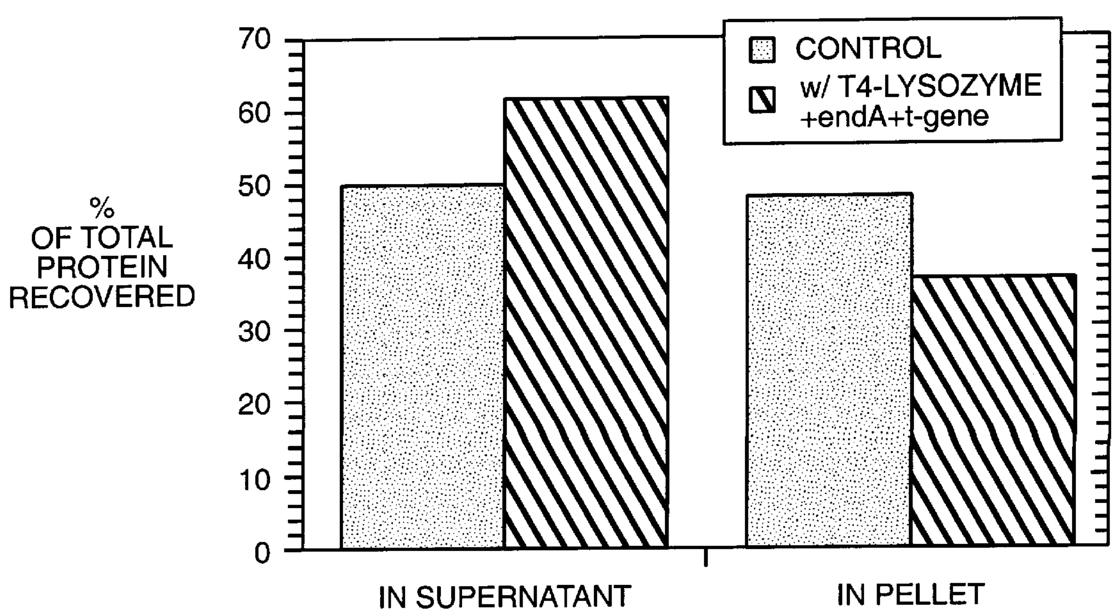
*FIG._10B*

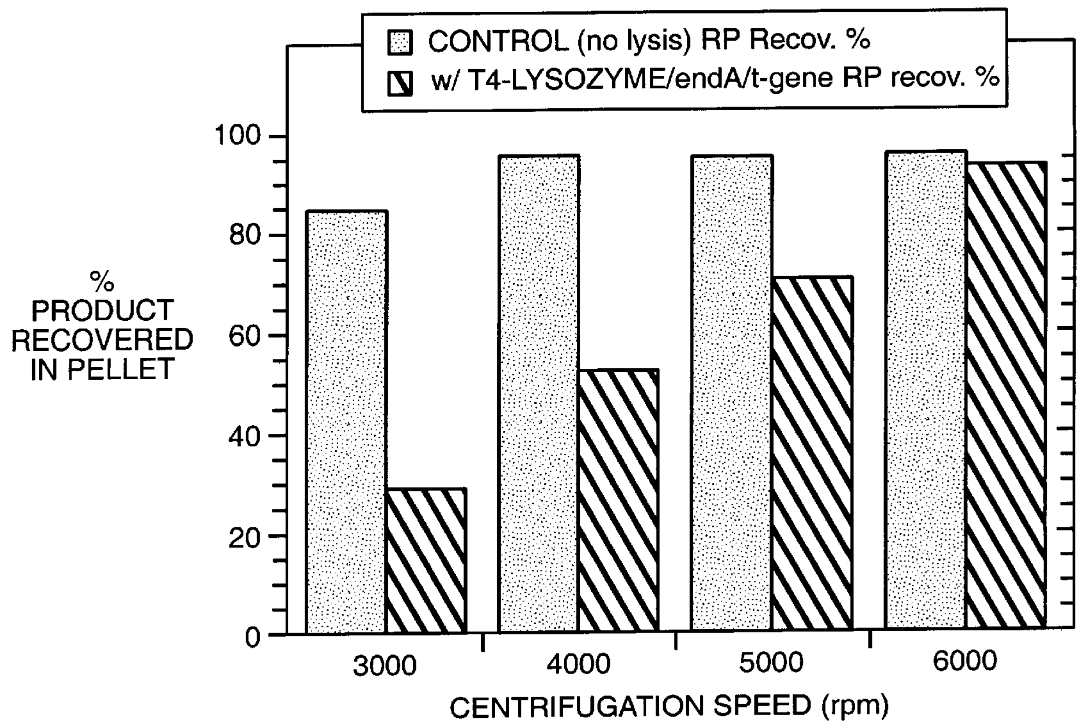
FIG._11
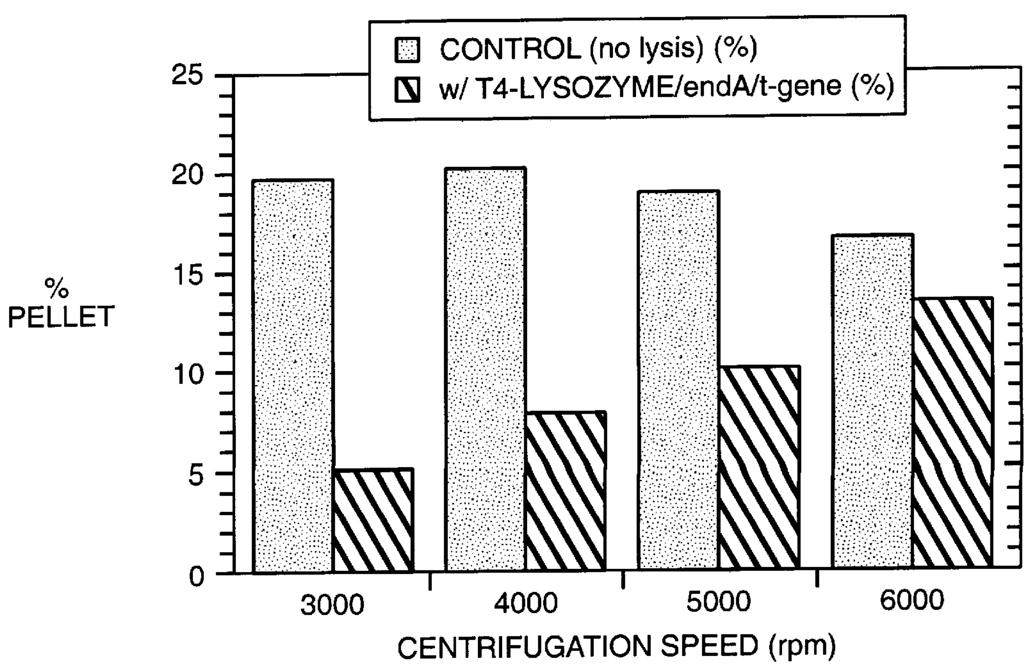
FIG._12

PROCESS FOR BACTERIAL PRODUCTION OF POLYPEPTIDES

RELATED APPLICATIONS

This application is a non-provisional application filed under 37 CFR 1.53(b) (1), claiming priority under 35 USC 119(e) to provisional application no. 60/106,052 filed Oct. 28, 1998, the contents of which are incorporated herein by reference.

BACKGROUND OF THE INVENTION

1. Field of the Invention

This invention relates to a process for producing and recovering heterologous polypeptides from bacterial cells. More particularly, this invention relates to a process wherein recovery of soluble or aggregated recombinant heterologous polypeptides from bacterial cytoplasm and periplasm is facilitated or increased.

2. Description of Related Disclosures

*Escherichia coli* has been widely used for the production of heterologous proteins in the laboratory and industry. *E. coli* does not generally excrete proteins to the extracellular medium apart from colicins and hemolysin (Pugsley and Schwartz, FEMS (Federation of European Microbiological Societies) Microbiology Reviews, 32: 3–38 (1985)). Heterologous proteins expressed by *E. coil* may accumulate as soluble product or insoluble aggregates. See FIG. 1 herein. They may be found intracellularly in the cytoplasm or be secreted into the periplasm if preceded by a signal sequence. How one proceeds initially in the recovery of the products greatly depends upon how and where the product accumulates. Generally, to isolate the proteins, the cells may be subjected to treatments for periplasmic extraction or be disintegrated to release trapped products that are otherwise inaccessible.

The conventional isolation of heterologous polypeptide from gram-negative bacteria poses problems owing to the tough, rigid cell walls that surround these cells. The bacterial cell wall maintains the shape of the cell and protects the cytoplasm from osmotic pressures that may cause cell lysis; it performs these functions as a result of a highly cross-linked peptidoglycan (also known as murein) backbone that gives the wall its characteristic rigidity. A recent model described the space between the cytoplasmic and outer membranes as a continuous phase filled with an inner periplasmic polysaccharide gel that extends into an outer highly cross-linked peptidoglycan gel (Hobot et al., *J. Bact.*, 160: 143 (1984)). This peptidoglycan sacculus constitutes a barrier to the recovery of any heterologous polypeptide not excreted by the bacterium into the medium.

To release recombinant proteins from the *E. coli* periplasm, treatments involving chemicals such as chloroform (Ames et al., *J. Bacteriol.*, 160: 1181–1183 (1984)), guanidine-HCl, and Triton X-100 (Naglak and Wang, *Enzyme Microb. Technol.*, 12: 603–611 (1990)) have been used. However, these chemicals are not inert and may have detrimental effects on many recombinant protein products or subsequent purification procedures. Glycine treatment of *E. coli* cells, causing permeabilization of the outer membrane, has also been reported to release the periplasmic contents (Ariga et al., *J. Ferm. Bioeng.*, 68: 243–246 (1989)). These small-scale per plasmic release methods have been designed for specific systems. They do not translate easily and efficiently and are generally unsuitable as large-scale methods.

The most widely used methods of periplasmic release of recombinant protein are osmotic shock (Nossal and Heppel, *J. Biol. Chem.*, 241: 3055–3062 (1966); Neu and Heppel, *J. Biol. Chem.*, 240: 3685–3692 (1965)), hen eggwhite (HEW)-lysozyme/ethylenediamine tetraacetic acid (EDTA) treatment (Neu and Heppel, *J. Biol. Chem.*, 239: 3893–3900 (1964); Witholt et al., *Biochim. Biophys. Acta*, 443: 534–544 (1976); Pierce et al., *ICheme Research Event*, 2: 995–997 (1995)), and combined HEW-lysozyme/osmotic shock treatment (French et al., *Enzyme and Microb. Tech.*, 19: 332–338 (1996)). Typically, these procedures include an initial disruption in osmotically-stabilizing medium followed by selective release in non-stabilizing medium. The composition of these media (pH, protective agent) and the disruption methods used (chloroform, HEW-lysozyme, EDTA, sonication) vary among specific procedures reported. A variation on the HEW-lysozyme/EDTA treatment using a dipolar ionic detergent in place of EDTA is discussed by Stabel et al., *Veterinary Microbiol.*, 38: 307–314 (1994). For a general review of use of intracellular lytic enzyme systems to disrupt *E. coli*, see Dabora and Cooney in *Advances in Biochemical Engineering/Biotechnology*, Vol. 43, A. Fiechter, ed. (Springer-Verlag: Berlin, 1990), pp. 11–30.

Conventional methods for the recovery of recombinant protein from the cytoplasm, as soluble protein or retractile particles, involved disintegration of the bacterial cell by mechanical breakage. Mechanical disruption typically involves the generation of local cavitation in a liquid suspension, rapid agitation with rigid beads, sonication, or grinding of cell suspension (*Bacterial Cell Surface Techniques*, Hancock and Poxton (John Wiley & Sons Ltd, 1988), Chapter 3, p. 55). These processes require significant capital investment and constitute long processing time.

HEW-lysozyme acts biochemically to hydrolyze the peptidoglycan backbone of the cell wall. The method was first developed by Zinder and Arndt, *Proc. Natl. Acad. Sci. USA*, 42: 586–590 (1956), who treated *E. coli* with egg albumin (which contains HEW-lysozyme) to produce rounded cellular spheres later known as spheroplasts. These structures retained some cell-wall components but had large surface areas in which the cytoplasmic membrane was exposed.

U.S. Pat. No. 5,169,772 discloses a method for purifying heparinase from bacteria comprising disrupting the envelope of the bacteria in an osmotically-stabilized medium, e.g., 20% sucrose solution using, e.g., EDTA, lysozyme, or an organic compound, releasing the non-heparinase-like proteins from the periplasmic space of the disrupted bacteria by exposing the bacteria to a low-ionic-strength buffer, and releasing the heparinase-like proteins by exposing the low-ionic-strength-washed bacteria to a buffered salt solution.

There are several disadvantages to the use of the HEW-lysozyme addition for isolating periplasmic proteins. The cells must be treated with EDTA, detergent, or high pH, all of which aid in weakening the cells. Also, the method is not suitable for lysis of large amounts of cells because the lysozyme addition is inefficient and there is difficulty in dispersing the enzyme throughout a large pellet of cells.

Many different modifications of these methods have been used on a wide range of expression systems with varying degrees of success (Joseph-Liauzun et al., *Gene*, 86: 291–295 (1990); Carter et al., *Bio/Technology*, 10: 163–167 (1992)). Although these methods have worked on a laboratory scale, they involve too many steps for an efficient large-scale recovery process.

Efforts to induce recombinant cell culture to produce lysozyme have been reported. EP 155,189 discloses a means for inducing a recombinant cell culture to produce lysozymes, which would ordinarily be expected to kill such host cells by means of destroying or lysing the cell wall structure. Russian Pat. Nos. 2043415, 2071503, and 2071501 disclose plasmids and corresponding strains for producing recombinant proteins and purifying water-insoluble protein agglomerates involving the lysozyme gene. Specifically, the use of an operon consisting of the lysozyme gene and a gene that codes for recombinant protein enables concurrent synthesis of the recombinant protein and a lysozyme that breaks the polysaccharide membrane of *E. coli*.

U.S. Pat. No. 4,595,658 discloses a method for facilitating externalization of proteins transported to the periplasmic space of *E. coli*. This method allows selective isolation of proteins that locate in the periplasm without the need for lysozyme treatment, mechanical grinding, or osmotic shock treatment of cells. U.S. Pat. No. 4,637,980 discloses producing a bacterial product by transforming a temperature-sensitive lysogen with a DNA molecule that codes, directly or indirectly, for the product, culturing the transformant under permissive conditions to express the gene product intracellularly, and externalizing the product by raising the temperature to induce phage-encoded functions. JP 61–257931 published Nov. 15, 1986 discloses a method for recovering IL-2 using HEW-lysozyme. Asami et al., *J. Ferment. and Bioeng.*, 83: 511–516 (1997) discloses synchronized disruption of *E. coli* cells by T4 phage infection, and Tanji et al., *J. Ferment. and Bioeng.*, 85: 74–78 (1998) discloses controlled expression of lysis genes encoded in T4 phage for the gentle disruption of *E. coli* cells.

The development of an enzymatic release method to recover recombinant periplasmic proteins suitable for large-scale use is reported by French et al., *Enzyme and Microbial Technology*, 19: 332–338 (1996). This method involves resuspension of the cells in a fractionation buffer followed by recovery of the periplasmic fraction, where osmotic shock immediately follows lysozyme treatment. The effects of overexpression of the recombinant protein, *S. thermoviolaceus* α-amylase, and the growth phase of the host organism on the recovery are also discussed.

In a 10-kiloliter-scale process for recovery of IGF-I polypeptide (Hart et al., *Bio/Technology*, 12: 1113 (1994)), the authors attempted the typical isolation procedure involving a mechanical cell breakage step followed by a centrifugation step to recover the solids. The results were disappointing in that almost 40% of the total product was lost to the supernatant after three passes through the Gaulin homogenizer. Hart et al., *Bio/Technology* 12: 1113 (1994). See FIG. 2 herein. Product recovery was not significantly improved even when the classical techniques of EDTA and HEW-lysozyme additions were employed.

While HEW-lysozyme is the only practical commercial lysozyme for large-scale processes, lysozyme is expressed by bacteriophages upon infection of host cells. Lysis of *E. coli*, a natural host for bacteriophages, for example the T4 phages, requires the action of two gene products: e and t. Gene e encodes a lysozyme (called T4-lysozyme for the T4 phage) that has been identified as a muramidase (Tsugita and Inouye, *J. Biol. Chem.*, 243: 391 (1968)), while gene t seems to be required for lysis, but does not appear to have lysozyme activity. Gene t is required for the cessation of cellular metabolism that occurs during lysis (Mukai et al., *Vir.*, 33: 398 (1967)) and is believed to degrade or alter the cytoplasmic membrane, thus allowing gene product e to reach the periplasm and gain access to the cell wall (Josslin, *Vir.*, 40: 719 (1970)). Phage are formed by gene t- mutants, but lysis of the *E. coli* host does not occur except by addition of chloroform (Josslin, supra). Wild-type T4-lysozyme activity is first detected about eight minutes after T4 infection at 37° C., and it increases through the rest of the infection, even if lysis inhibition is induced. In the absence of secondary adsorption, cells infected by gene e mutants shut down progeny production and metabolism at the normal time, but do not lyse (*Molecular Genetics of Bacteriophage* T4, J. D. Karam, ed. in chief (American Society for Microbiology, Washington D.C., ASM Press, 1994), p. 398).

Recovery of insoluble IGF-I using T4-lysozyme was disclosed on Oct. 28, 1997 at the "Separation Technology VII meeting entitled 'Separations for Clean Production'" in Davos, Switzerland, sponsored by the Engineering Foundation.

Upon cell lysis, genomic DNA leaks out of the cytoplasm into the medium and results in significant increase in fluid viscosity that can impede the sedimentation of solids in a centrifugal field. In the absence of shear forces such as those exerted during mechanical disruption to break down the DNA polymers, the slower sedimentation rate of solids through viscous fluid results in poor separation of solids and liquid during centrifugation. Other than mechanical shear force, there exist nucleolytic enzymes that degrade DNA polymer. In *E. coli*, the endogenous gene endA encodes for an endonuclease (molecular weight of the mature protein is approx. 24.5 kD) that is normally secreted to the periplasm and cleaves DNA into oligodeoxyribonucleotides in an endonucleolytic manner. It has been suggested that endA is relatively weakly expressed by *E. coli* (Jekel and Wackernagel et al., *Gene*, 154: 55–59 (1995)).

For controlling cost of goods and minimizing process time, there is a continuing need for increasing the total recovery of heterologous polypeptide from cells. At large scale, there is a significant incentive to avoid mechanical cell breakage to release the soluble or aggregated recombinant polypeptide from the cytoplasmic and periplasmic compartments and to condition the lysate for efficient product recovery in the subsequent step.

SUMMARY OF THE INVENTION

Accordingly, this invention provides processes using biochemical disruption to recover both soluble and insoluble heterologous product from bacterial cells.

In one aspect the present invention provides a process for recovering a heterologous polypeptide from bacterial cells comprising:

(a) culturing bacterial cells, which cells comprise nucleic acid encoding phage lysozyme and nucleic acid encoding a protein that displays DNA-digesting activity under the control of a signal sequence for secretion of said DNA-digesting protein, wherein said nucleic acids are linked to a first promoter, and nucleic acid encoding the heterologous polypeptide and a signal sequence for secretion of the heterologous polypeptide, which nucleic acid encoding the heterologous polypeptide is linked to a second promoter, wherein the second promoter is inducible and the first promoter is either a promoter with low basal expression or an inducible promoter, the culturing being under conditions whereby when an inducer is added, expression of the nucleic acid encoding the phage lysozyme and DNA-digesting protein is induced after about 50% or more of the heterologous polypeptide has accumulated, whereby the phage lysozyme accumulates in a cytoplasmic compartment, whereby the DNA-digesting protein is secreted to the periplasm, and whereby the cells are lysed to produce a broth lysate; and (b) recovering accumulated heterologous polypeptide from the broth lysate.

In yet another aspect, the invention supplies a process for recovering a heterologous polypeptide from bacterial cells in which it is produced comprising:

(a) culturing the bacterial cells, which cells comprise nucleic acid encoding phage lysozyme, gene t, and nucleic acid encoding a protein that displays DNA-digesting activity, wherein these nucleic acids are linked to a first promoter, and nucleic acid encoding the heterologous polypeptide, which nucleic acid is linked to a second promoter, wherein the second promoter is inducible and the first promoter is either a promoter with low basal expression or an inducible promoter, the culturing being under conditions whereby when an inducer is added, expression of the nucleic acids encoding the phage lysozyme, gene t, and DNA-digesting protein is induced after about 50% or more of the heterologous polypeptide has accumulated, and under conditions whereby the phage lysozyme accumulates in a cytoplasmic compartment, whereby the DNA-digesting protein is secreted into the periplasm, and whereby the cells are lysed to produce a broth lysate; and (b) recovering accumulated heterologous polypeptide from the broth lysate.

In a third aspect, the invention provides a process for recovering a heterologous polypeptide from bacterial cells in which it is produced comprising:

(a) culturing the bacterial cells, which cells comprise nucleic acid encoding phage lysozyme, gene t, and nucleic acid encoding a protein that displays DNA-digesting activity, wherein the nucleic acid encoding the phage lysozyme and DNA-digesting protein is linked to a first promoter that is inducible or with low basal expression, the gene t is linked to a second inducible promoter, and the nucleic acid encoding the heterologous polypeptide is linked to a third inducible promoter, under conditions whereby when an inducer is added and all three promoters are inducible, expression of the nucleic acids encoding the phage lysozyme, gene t, and DNA-digesting protein is induced after about 50% or more of the heterologous polypeptide has accumulated, with the third promoter being induced before the first promoter and the second promoter induced after the first promoter, and whereby if the phage lysozyme and DNA-digesting protein are linked to a promoter with low basal expression, expression of the gene t is induced after about 50% or more of the heterologous polypeptide has accumulated, and under conditions whereby the phage lysozyme accumulates in a cytoplasmic compartment, whereby the DNA-digesting protein is secreted into the periplasm, and whereby the cells are lysed to produce a broth lysate; and (b) recovering accumulated heterologous polypeptide from the broth lysate.

Biochemical lysis or biochemically-assisted mechanical lysis is superior to mechanical disruption for recovering heterologous polypeptide from bacterial cells. Coordinated expression of nucleic acid encoding phage lysozyme with gene t and DNA-digesting protein, and nucleic acid encoding the heterologous polypeptide of interest provides a highly effective method for releasing insoluble or soluble polypeptide from the entanglement with the peptidoglycan layer, as well as releasing product trapped in the cytoplasm. When the phage lysozyme gene is cloned behind a tightly-controlled promoter, for example, the pBAD promoter (also referred to as the ara promoter), cytoplasmic accumulation of phage lysozyme may be induced by the addition of an inducer (such as arabinose) at an appropriate time near the end of fermentation. By placing the nucleic acid expression of heterologous polypeptide and lytic enzymes under separate promoter control, one can independently regulate their production during fermentation. Without a signal sequence, the accumulated phage lysozyme is tightly locked up in the cytoplasmic compartment, and gene t functions to release the phage lysozyme to degrade the peptidoglycan layer. Furthermore, the optimal pH for T4-phage-lysozyme activity, which is a preferred embodiment, is about 7.3, which is about the neutral pH of most typical harvest broths.

The induction of the genes encoding the bacteriophage lysozyme, DNA-digesting protein, and gene t after expression of the nucleic acid encoding the heterologous polypeptide results in a significant amount of insoluble or soluble heterologous polypeptide recovered from the cytoplasm or periplasm of bacteria. Besides product yield, the success of a recovery process is judged by the ease of operation, the process flow, the turn-around time, as well as the operation cost. The present invention alleviates several if not all these bottlenecks encountered in the large-scale recovery process.

The processes herein also allow use of biochemical cell lysis at high cell density and increased scale. At high density, excessive expression of T4-lysozyme, gene t, and endA could have disastrous results, such as premature cell lysis and reduction in heterologous polypeptide production. Further, it would not be expected that induction at the end of a long fermentation process and after substantial product accumulation would produce enough of the lytic enzymes to be effective. The present processes do not pose problems at high cell densities such as increased viscosity and excessive foaming during the fermentation process. It is expected that the processes herein will enable the attainment of high cell density, effective induction and action of the system, and the processing of broth lysates derived from high-density cultures.

BRIEF DESCRIPTION OF THE DRAWINGS

FIG. 1 depicts a schematic diagram of how a polypeptide product is disposed in the cytoplasm and in the periplasm, that is, it forms an aggregate, proteolyzed fragment, or folded soluble polypeptide.

FIG. 2 depicts IGF-I aggregate recovery from the supernatant and pellet by the typical isolation procedure involving mechanical cell disruption followed by centrifugation, after three passes through the Gaulin homogenizer.

FIG. 3 depicts a plasmid map of pS1130, an expression plasmid for rhuMAb CD18 F(ab')$_2$-leucine zipper precursor (herein also referred to as anti-CD18 antibody fragment).

FIGS. 4A-1, 4A-2, 4B-1 and 4B-2 show the sequence of the expression cassette of pS1130 (SEQ ID NOS:1, 2 and 3).

FIG. 5 shows plasmid construction of pJJ154 used to co-express T4-lysozyme and endA (*E. coli* DNase).

FIG. 6 shows a plasmid map of pLBIGF57 used to express IGF-I.

FIG. 7 shows plasmid construction of pJJ155 used to express T4-lysozyme, endA, and gene t, which construction is from pJJ154.

FIG. 8 depicts a schematic of the two-plasmid system for co-expression of T4-lysozyme, a preferred phage lysozyme, endA, a preferred DNA-digesting protein, and gene t (pJJ155) with IGF-I-encoding nucleic acid in accordance with an example of this invention.

FIGS. 9A–9E disclose photographs from phase-contrast microscopy of the harvest broth and resuspended pellets from centrifugation of fermentation broth with and without co-expression of T4-lysozyme and endA and t-gene before and after EDTA addition. Specifically, the photographs show the resuspended pellet from centrifugation of control broth with no lytic enzyme co-expression before and after EDTA addition respectively (FIGS. 9A and 9B), the fermentation harvest undiluted whole broth resulting from co-expression of IGF-I with the three lytic enzymes, T4-lysozyme, endA, and t-gene (FIG. 9C), the resuspended pellet from centrifugation of harvest broth with co-expression of IGF-I with the three lytic enzymes and no EDTA addition (FIG. 9D), and the resuspended pellet from centrifugation of harvest broth with the co-expression of IGF-I with the three lytic enzymes and EDTA addition (FIG. 9E).

FIGS. 10A and 10B show, respectively, nucleic acid quantitation in the supernatant and pellet by OD260 determination for IGF-I-expressing *E. coli* with co-expression of the three lytic enzymes versus control, and total protein in the supernatant and pellet from IGF-I-expressing *E. coli* with co-expression of the three lytic enzymes versus no co-expression control.

FIG. 11 shows IGF-I product recovery by centrifugation using three lytic enzymes versus no-lysis control broth for various centrifugation speeds.

FIG. 12 shows solids recovery during centrifugation using three lytic enzymes co-expressed with IGF-I versus no-lysis control broth for various centrifugation speeds.

DETAILED DESCRIPTION OF THE PREFERRED EMBODIMENTS

A. Definitions

As used herein, "phage lysozyme" refers to a cytoplasmic enzyme that facilitates lysis of phage-infected bacterial cells, thereby releasing replicated phage particles. The lysozyme may be from any bacteriophage source, including T7, T4, lambda, and mu bacteriophages. The preferred such lysozyme herein is T4-lysozyme.

As used herein, "T4-lysozyme" or "E protein" refers to a cytoplasmic muramidase that facilitates lysis of T4 phage-infected bacterial cells, thereby releasing replicated phage particles (Tsugita and Inouye, *J. Mol. Biol.*, 37: 201–12 (1968); Tsugita and Inouye, *J. Biol. Chem.*, 243: 391–97 (1968)). It is encoded by gene e of T4 bacteriophage and hydrolyzes bonds between N-acetylglucosamine and N-acetylmuramic acid residues in the rigid peptidoglycan layer of the *E. coli* cell envelope. The enzyme is a single polypeptide chain of a molecular weight of 18.3 kd. It is approximately 250-fold more active than HEW-lysozyme against bacterial peptidoglycan (Matthews et al., *J. Mol. Biol.*, 147: 545–558 (1981)). The optimal pH for T4-lysozyme enzyme activity is 7.3, versus 9 for HEW-lysozyme (*The Worthington Manual*; pp 219–221).

As used herein, "gene t" or "t gene" or "holin" refers to a lytic gene of bacteriophage T4 that is required for lysis but does not appear to have lysozyme activity. See also *Molecular Genetics of Bacteriophage* T4, supra, p. 398–399.

The term "protein that displays DNA-digesting activity" or "DNA-digesting protein" refers to a protein that will digest DNA such as, for example, mammalian or bacterial DNase. Preferably, the DNA-digesting protein is human DNase or bacterial endA.

As used herein, the phrase "lytic enzymes" refers collectively to at least phage lysozyme and DNA-digesting protein; where applicable it also refers to a phage gene t gene product or equivalent in combination with phage lysozyme and DNA-digesting protein.

As used herein, the phrase "agent that disrupts the outer cell wall" of bacteria refers to a molecule that increases permeability of the outer cell wall of bacteria, such as chelating agents, e.g., EDTA, and zwitterions.

As used herein, the term "bacteria" refers to any bacterium that produces proteins that are transported to the periplasmic space. Generally, the bacteria, whether gram positive or gram negative, has phage lysozyme and nuclease expression under control so that they are only expressed near the end of the fermentation, a preferred embodiment, or expressed at a low level during fermentation. The nuclease is generally relatively stable when secreted to the periplasm or medium. The term "non-temperature-sensitive bacteria" refers to any bacterium that is not significantly sensitive to temperature changes. One preferred embodiment herein is bacteria that are not temperature sensitive. The most preferred bacteria herein are gram-negative bacteria.

As used herein, "a time sufficient to release the polypeptide contained in the cytoplasm or periplasm" refers to an amount of time sufficient to allow the lysozyme to digest the peptidoglycan to a sufficient degree to release the cytoplasmic or periplasmic aggregate or soluble heterologous polypeptide.

As used herein, "signal sequence" or "signal polypeptide" refers to a peptide that can be used to secrete the heterologous polypeptide or protein that displays DNA-digesting activity into the periplasm of the bacteria. The signals for the heterologous polypeptide or DNA-digesting protein may be homologous to the bacteria, or they may be heterologous, including signals native to the heterologous polypeptide or DNA-digesting protein being produced in the bacteria.

The promoters of this invention may be "inducible" promoters, i.e., promoters that direct transcription at an increased or decreased rate upon binding of a transcription factor.

As used herein, a promoter "with low basal expression" or a "low-basal-expression promoter" is a promoter that is slightly leaky, i.e., it provides a sufficiently low basal expression level so as not to affect cell growth or product accumulation and provides a sufficiently low level of promotion not to result in premature cell lysis. "Transcription factors" as used herein include any factors that can bind to a regulatory or control region of a promoter and thereby effect transcription. The synthesis or the promoter-binding ability of a transcription factor within the host cell can be controlled by exposing the host to an "inducer" or removing a "repressor" from the host cell medium. Accordingly, to regulate expression of an inducible promoter, an inducer is added or a repressor removed from the growth medium of the host cell.

As used herein, the phrase "induce expression" means to increase the amount of transcription from specific genes by exposure of the cells containing such genes to an effector or inducer.

An "inducer" is a chemical or physical agent which, when given to a population of cells, will increase the amount of transcription from specific genes. These are usually small molecules whose effects are specific to particular operons or groups of genes, and can include sugars, alcohol, metal ions, hormones, heat, cold, and the like. For example, isopropylthio-β-galactoside (IPTG) and lactose are inducers of the tacII promoter, and L-arabinose is a suitable inducer of the arabinose promoter.

A "repressor" is a factor that directly or indirectly leads to cessation of promoter action or decreases promoter action. One example of a repressor is phosphate. As the repressor phosphate is depleted from the medium, the alkaline phosphatase (AP) promoter is induced.

As used herein, "polypeptide" or "polypeptide of interest" refers generally to peptides and proteins having more than about ten amino acids. The polypeptides are "heterologous," i.e., foreign to the host cell being utilized, such as a human protein produced by *E. coli*. The polypeptide may be produced as an insoluble aggregate or as a soluble polypeptide in the periplasmic space or cytoplasm.

Examples of mammalian polypeptides include molecules such as, e.g., renin, a growth hormone, including human growth hormone; bovine growth hormone; growth hormone releasing factor; parathyroid hormone; thyroid stimulating hormone; lipoproteins; α1-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and—beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF-β; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1–3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; anti-HER-2 antibody; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

The preferred exogenous polypeptides of interest are mammalian polypeptides, most preferably human polypeptides. Examples of such mammalian polypeptides include t-PA, VEGF, gp120, anti-HER-2, anti-CD11a, anti-CD18, DNase, IGF-I, IGF-II, brain IGF-I, growth hormone, relaxin chains, growth hormone releasing factor, insulin chains or pro-insulin, urokinase, immunotoxins, neurotrophins, and antigens. Particularly preferred mammalian polypeptides include, e.g., IGF-I, DNase, or VEGF, most preferably IGF-I, if the polypeptide is produced as an insoluble aggregate in the periplasm, and anti-CD18 antibodies or fragments thereof such as anti-recombinant human CD18 Fab, Fab' and $(Fab')_2$ fragments, if the polypeptide is produced in a soluble form in the periplasm.

As used herein, "IGF-I" refers to insulin-like growth factor from any species, including bovine, ovine, porcine, equine, and preferably human, in native-sequence or in variant form and recombinantly produced. In a preferred method, the IGF-I is cloned and its DNA expressed, e.g., by the process described in EP 128,733 published Dec. 19, 1984.

The expression "control sequences" refers to DNA sequences necessary for the expression of an operably-linked coding sequence in a particular host organism. The control sequences that are suitable for bacteria include a promoter such as the alkaline phosphatase promoter, optionally an operator sequence, and a ribosome-binding site.

Nucleic acid is "operably linked" when it is placed into a functional relationship with another nucleic acid sequence. For example, DNA for a presequence or secretory leader is operably linked to DNA for a heterologous polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading frame. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

B. Modes for Carrying Out the Invention

In one embodiment, the invention provides a process for recovering a heterologous polypeptide, soluble or insoluble, from bacterial cells in which it is produced. This process involves, in a first step, culturing the bacterial cells, which cells comprise nucleic acid encoding the lytic enzymes, wherein these nucleic acids are linked to a first promoter, and nucleic acid encoding the heterologous polypeptide, which nucleic acid is linked to a second inducible promoter. In an alternative embodiment, the phage lysozyme and DNA-digesting protein are linked to a first inducible promoter or a promoter with low basal expression, the t-gene is linked to a second inducible promoter, and the heterologous polypeptide is linked to a third inducible promoter.

The culturing takes place under conditions whereby expression of the nucleic acids encoding the lytic enzymes, when induced, commences after about 50% or more of the heterologous polypeptide has accumulated, and under conditions whereby the phage lysozyme accumulates in a cytoplasmic compartment and the DNA-digesting protein is secreted into the periplasmic compartment.

In the processes herein, induction of the promoters is preferred; however, the processes also contemplate the use of a promoter for the phage lysozyme and DNA-digesting protein that is a promoter with low basal expression (slightly leaky), wherein no induction is carried out. This type of promoter has a leakiness that is low enough not to result in premature cell lysis and results in a sufficiently low basal expression level so as not to affect cell growth or product accumulation.

In a second step, the accumulated heterologous polypeptide is recovered from the bacterial cells. An agent that increases permeability of the outer cell wall of the bacterial cells may be added, as described in detail below, before the recovery step is carried out. The need to disrupt cells mechanically to release the phage lysozyme is either reduced or is completely avoided. In a preferred embodiment, after lytic enzyme expression the cells are incubated for a time sufficient to release the heterologous polypeptide contained in the cytoplasm or periplasm.

While the processes can apply to the recovery of insoluble aggregates such as IGF-I, VEGF, and DNase by sedimentation of product, they are also applicable to heterologous polypeptides that are soluble in the cytoplasm or periplasm, such as, for example, anti-CD18 antibody fragment. Advantages for recovery of soluble heterologous polypeptides by biochemical cell lysis include avoiding or reducing the need for mechanical lysis, thereby avoiding loss of heat-labile proteins, and obtaining a low and consistent fluid viscosity compatible with downstream recovery processes such as expanded bed absorption technology and centrifugation.

Expanded bed absorption (EBA) chromatography, described, for example, in "Expanded Bed Adsorption: Principles and Methods", *Pharmacia Biotech*, ISBN 91-630-5519-8), is useful for the initial recovery of target proteins from crude feed-stock or cell culture. The process steps of clarification, concentration, and initial purification can be combined into one unit operation, providing increased process economy due to a decreased number of process steps, increased yield, shorter overall process time, reduced labor cost, and reduced cost. In EBA chromatography an adsorbent is expanded and equilibrated by applying an upward liquid flow to the column. A stable fluidized bed is formed when the adsorbent particles are suspended in equilibrium due to the balance between particle sedimentation velocity and upward liquid flow velocity. Crude cell mixture or broth lysate is applied to the expanded bed with an upward flow. Target proteins are bound to the adsorbent while cell debris and other contaminants pass through unhindered. Weakly bound material is washed from the expanded bed using upward flow of a wash buffer. Flow is then stopped and the adsorbent is allowed to settle in the column. The column adaptor is then lowered to the surface of the sedimented bed. Flow is reversed and the captured proteins are eluted from the sedimented bed using an appropriate buffer. The eluate contains the target protein in a reduced elution pool volume, partially purified in preparation for packed bed chromatography (*Pharmacia Biotech*, supra). EBA, wherein the whole cell lysate containing soluble product is pumped up through the column and the protein is absorbed onto a resin (fluidized bed) and the cell debris flows through, utilizes only one chromatography step, thereby saving a step.

In another embodiment, the invention provides a process for recovering soluble heterologous polypeptide from the cytoplasm or periplasm of bacterial cells. This process involves culturing bacterial cells, which cells comprise nucleic acid encoding phage lysozyme and nucleic acid encoding a DNA-digesting protein that displays DNA-digesting activity under the control of a signal sequence for secretion of said DNA-digesting protein. In this process, the nucleic acids are linked to a first promoter, and nucleic acid encoding the heterologous polypeptide and a signal sequence for secretion of the heterologous polypeptide, which nucleic acid encoding the heterologous polypeptide is linked to a second inducible promoter. This culturing takes place under conditions whereby over-expression of the nucleic acid encoding the phage lysozyme and DNA-digesting protein is weakly and constitutively promoted or, if induced, commences after about 50% or more of the heterologous polypeptide has accumulated, and under conditions whereby the heterologous polypeptide and DNA-digesting protein are secreted into the periplasm of the bacteria and the phage lysozyme accumulates in a cytoplasmic compartment.

In a second step, the resulting heterologous polypeptide is recovered from the broth lysate.

In a third embodiment, the invention provides a process for recovering a heterologous polypeptide from bacterial cells in which three different promoters are used. Specifically, in the first step, the bacterial cells are cultured, where the cells comprise nucleic acid encoding phage lysozyme, gene t, and nucleic acid encoding a protein that displays DNA-digesting activity, as well as nucleic acid encoding the heterologous polypeptide. The nucleic acid encoding the lysozyme and DNA-digesting protein is linked to a first promoter that is inducible or with low basal expression, the gene t is linked to a second inducible promoter, and the nucleic acid encoding the heterologous polypeptide is linked to a third inducible promoter.

The culturing is carried out under conditions whereby when an inducer is added and all three promoters are inducible, expression of the nucleic acids encoding the phage lysozyme, gene t, and DNA-digesting protein is induced after about 50% or more of the heterologous polypeptide has accumulated, with the third promoter being induced before the first promoter, and the second promoter induced last, and whereby if the phage lysozyme and DNA-digesting protein are linked to a promoter with low basal expression, expression of the gene t is induced after about 50% or more of the heterologous polypeptide has accumulated. Culturing is also carried out under conditions whereby the phage lysozyme accumulates in a cytoplasmic compartment, whereby the DNA-digesting protein is secreted to and accumulates in the periplasm, and whereby the cells are lysed to produce a broth lysate.

In a second step, accumulated heterologous polypeptide is recovered from the broth lysate.

In the above processes, while the signal sequence for the DNA-digesting protein may be any sequence, preferably, it is a native sequence of the DNA-digesting protein. Also, in a preferred embodiment, the DNA-digesting protein is DNase or bacterial, e.g., *E. coli* endA product.

In a preferred embodiment, the culturing step takes place under conditions of high cell density, that is, generally at a cell density of about 15 to 150 g dry weight/liter, preferably at least about 40, more preferably about 40–150, most preferably about 40 to 100. In optical density, 120 OD550 ($A_{550}$) is about 50 g dry wt./liter. In addition, the culturing can be accomplished using any scale, even very large scales of 100,000 liters. Preferably, the scale is about 100 liters or greater, more preferably at least about 500 liters, and most preferably from about 500 liters to 100,000 liters.

The nucleic acids encoding the lytic enzymes are linked to one promoter, i.e., put in tandem, as by placing a linker between the nucleic acids. The promoter for the heterologous polypeptide expression is different from that used for the lytic enzymes, such that one is induced before the other. While the promoters may be any suitable promoters for this purpose, preferably, the promoters for the lytic enzymes with or without gene t and heterologous polypeptide are, respectively, arabinose promoter and alkaline phosphatase promoter.

The promoters for the heterologous polypeptide and for the lytic enzymes for all three processes herein must be different, such that the nucleic-acid-encoded heterologous polypeptide expression is induced before expression of nucleic-acid-encoded lytic enzymes or at a much higher level, when the promoters are inducible. While the promoters may be any suitable promoters for this purpose, preferably, the promoters for the phage lysozyme and heterologous polypeptide are, respectively, arabinose promoter and alkaline phosphatase promoter. Alternatively, the compartmentalization of the phage lysozyme and DNA-digesting protein may allow for the use of a promoter with low basal expression for expression of the nucleic acid encoding phage lysozyme and DNA-digesting protein. If a promoter with low basal expression is employed, such as arabinose as opposed to tac or trp promoter, then an active step of induction is not required.

The induction of expression of the nucleic acid encoding the lytic enzymes is preferably carried out by adding an inducer to the culture medium. While, in this respect, the inducers for the promoters may be added in any amount, preferably if the inducer is arabinose, it is added in an amount of about 0–1% by weight, and if inducer is added, 0.1–1% by weight.

In the processes described above, typically the expression elements are introduced into the cells by transformation therein, but they may also be integrated into the genome or chromosome of the cells along with their promoter regions. This applies to any of the lytic enzymes or the heterologous polypeptide gene. The bacterial cells may be transformed with one or more expression vectors containing the nucleic acid encoding the lytic enzymes, and the nucleic acid encoding the heterologous polypeptide. In one such embodiment, the bacterial cells are transformed with two vectors respectively containing the nucleic acid encoding the lytic enzymes and the nucleic acid encoding the heterologous polypeptide. In another embodiment, the nucleic acid encoding the lytic enzymes and the nucleic acid encoding the heterologous polypeptide are contained on one vector with which the bacterial cells are transformed. In another specific embodiment that may be preferred, the phage lysozyme and DNA-digesting enzyme are carried on a plasmid to ensure high copy number and the gene t is integrated into the host chromosome to down-regulate expression and prevent premature cell lysis to avoid leakiness.

In the first step of the above processes, the heterologous nucleic acid (e.g., cDNA or genomic DNA) is suitably inserted into a replicable vector for expression in the bacterium under the control of a suitable promoter for bacteria. Many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation may include a signal sequence for the heterologous polypeptide and will include a signal sequence for the DNA-digesting protein and will also include an inducible promoter for the heterologous polypeptide and gene t and an inducible promoter or a non-inducible one with low basal expression for the other lytic enzymes. They also generally include an origin of replication and one or more marker genes.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, *E. coli* is typically transformed using pBR322, a plasmid derived from an *E. coli* species. See, e.g., Bolivar et al., *Gene*, 2: 95 (1977). pBR322 contains genes conferring ampicillin and tetracycline resistance and thus provides an easy means for identifying transformed cells. The pBR322 plasmid, or other microbial plasmid or phage, also generally contains, or is modified to contain, promoters that can be used by the bacterial organism for expression of the selectable marker genes.

If the heterologous polypeptide is to be secreted, the DNA encoding the heterologous polypeptide of interest herein contains a signal sequence, such as one at the N-terminus of the mature heterologous polypeptide. In general, the signal sequence may be a component of the vector, or it may be a part of the heterologous polypeptide DNA that is inserted into the vector. The heterologous signal sequence selected should be one that is recognized and processed (i.e., cleaved by a signal peptidase) by the host cell. For bacterial host cells that do not recognize and process the native heterologous polypeptide signal sequence, the signal sequence is substituted by a bacterial signal sequence selected, for example, from the group consisting of the alkaline phosphatase, penicillinase, lpp, or heat-stable enterotoxin II leaders.

Expression vectors contain a nucleic acid sequence that enables the vector to replicate in one or more selected host cells. Such sequences are well known for a variety of bacteria. The origin of replication from the plasmid pBR322 is suitable for most Gram-negative bacteria.

Expression vectors also generally contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen.

The expression vector for producing a heterologous polypeptide also contains an inducible promoter that is recognized by the host bacterial organism and is operably linked to the nucleic acid encoding the heterologous polypeptide of interest. It also contains a separate inducible or low-basal-expression promoter operably linked to the nucleic acid encoding the lytic enzymes. Inducible promoters suitable for use with bacterial hosts include the β-lactamase and lactose promoter systems (Chang et al., *Nature*, 275: 615 (1978); Goeddel et al., *Nature*, 281: 544 (1979)), the arabinose promoter system, including the araBAD promoter (Guzman et al., *J. Bacteriol.*, 174: 7716–7728 (1992); Guzman et al., *J. Bacteriol.*, 177: 4121–4130 (1995); Siegele and Hu, *Proc. Natl. Acad. Sci. USA*, 94: 8168–8172 (1997)), the rhamnose promoter (Haldimann et al., *J. Bacteriol.*, 180: 1277–1286 (1998)), the alkaline phosphatase promoter, a tryptophan (trp) promoter system (Goeddel, *Nucleic Acids Res.*, 8: 4057 (1980) and EP 36,776), the $P_{LtetO-1}$ and $P_{lac/are-1}$ promoters (Lutz and Bujard, *Nucleic Acids Res.*, 25: 1203–1210 (1997)), and hybrid promoters such as the tac promoter. deBoer et al.,

*Proc. Nati. Acad. Sci. USA*, 80: 21–25 (1983). However, other known bacterial inducible promoters and low-basal-expression promoters are suitable. Their nucleotide sequences have been published, thereby enabling a skilled worker operably to ligate them to DNA encoding the heterologous polypeptide of interest or to the nucleic acids encoding the lytic enzymes (Siebenlist et al., *Cell*, 20: 269 (1980)) using linkers or adaptors to supply any required restriction sites. If a strong and highly leaky promoter, such as the trp promoter, is used, it is generally used only for expression of the nucleic acid encoding the heterologous polypeptide and not for lytic-enzyme-encoding nucleic acid. The tac and $P_L$ promoters could be used for either, but not both, the heterologous polypeptide and the lytic enzymes, but are not preferred. Preferred are the alkaline phosphatase promoter for the product and the arabinose promoter for the lytic enzymes.

Promoters for use in bacterial systems also generally contain a Shine-Dalgarno (S.D.) sequence operably linked to the DNA encoding the heterologous polypeptide of interest. The promoter can be removed from the bacterial source DNA by restriction enzyme digestion and inserted into the vector containing the desired DNA. The phoA promoter can be removed from the bacterial- source DNA by restriction enzyme digestion and inserted into the vector containing the desired DNA.

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform *E. coli* K12 strain 294 (ATCC 31,446) or other strains, and successful transformants are selected by ampicillin or tetracycline resistance where appropriate. Plasmids from the transformants are prepared, analyzed by restriction endonuclease digestion, and/or sequenced by the method of Sanger et al., *Proc. Natl. Acad. Sci. USA*, 74: 5463–5467 (1977) or Messing et al., *Nucleic Acids Res.*, 9: 309 (1981), or by the method of Maxam et al., *Methods in Enzymology*, 65: 499 (1980).

Suitable bacteria for this purpose include archaebacteria and eubacteria, especially eubacteria, more preferably Gram-negative bacteria, and most preferably Enterobacteriaceae. Examples of useful bacteria include Escherichia, Enterobacter, Azotobacter, Erwinia, Bacillus, Pseudomonas, Klebsiella, Proteus, Salmonella, Serratia, Shigella, Rhizobia, Vitreoscilla, and Paracoccus. Suitable *E. coli* hosts include *E. coli* W3110 (ATCC 27,325), *E. coli* 294 (ATCC 31,446), *E. coli* B, and *E. coli* X1776 (ATCC 31,537). These examples are illustrative rather than limiting. Mutant cells of any of the above-mentioned bacteria may also be employed. It is, of course, necessary to select the appropriate bacteria taking into consideration replicability of the replicon in the cells of a bacterium. For example, *E. coli*, Serratia, or Salmonella species can be suitably used as the host when well-known plasmids such as pBR322, pBR325, pACYC177, or pKN410 are used to supply the replicon.

*E. coli* strain W3110 is a preferred host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 1A2, which has the complete genotype tonAΔ (also known as ΔfhuA); *E. coli* W3110 strain 9E4, which has the complete genotype tonAΔ ptr3; *E. coli* W3110 strain 27C7 (ATCC 55,244), which has the complete genotype tonAΔ ptr3 phoAΔE15 Δ(argF-lac)169 ompTΔ degP41kan$^r$; *E. coli* W3110 strain 37D6, which has the complete genotype tonAΔ ptr3 phoAΔE15 Δ(argF-lac)169 ompTΔ degP41kan$^r$ rbs7Δ ilvg; *E. coli* W3110 strain 40B4, which is strain 37D6 with a non-kanamycin resistant degP deletion mutation; *E. coli* W3110 strain 33D3, which has the complete genotype tonA ptr3 lacIg LacL8 ompT degP kan$^r$; *E. coli* W3110 strain 36F8, which has the complete genotype tonA phoA Δ(argF-lac) ptr3 degP kan$^R$ ilvG+, and is temperature resistant at 37° C.; *E. coli* W3110 strain 45F8, which has the complete genotype fhuA(tonA) Δ(argF-lac) ptr3 degP41(kanS) Δ omp Δ(nmpc-fepE) ilvG+ phoA+ phoS*(T10Y); *E. coli* W3110 strain 33B8, which has the complete genotype tonA phoA Δ(argF-lac) 189 deoc degP IlvG+ (kanS); *E. coli* W3110 strain 43E7, which has the complete genotype fhuA(tonA) Δ(argF-lac) ptr3 degP41 (kanS) ΔompTΔ(nmpc-fepE) ilvG+ phoA+; and an *E. coli* strain having the mutant periplasmic protease(s) disclosed in U.S. Pat. No. 4,946,783 issued Aug. 7, 1990.

Host cells are transformed with the above-described expression is vectors of this invention and cultured in conventional nutrient media modified as appropriate for inducing the various promoters if induction is carried out.

Transformation means introducing DNA into an organism so that the DNA is replicable, either as an extrachromosomal element or as chromosomal integration. Depending on the host cell used, transformation is done using standard techniques appropriate to such cells. The calcium treatment employing calcium chloride, as described in section 1.82 of Sambrook et al., *Molecular Cloning: A Laboratory Manual* (New York: Cold Spring Harbor Laboratory Press, 1989), is generally used for bacterial cells that contain substantial cell-wall barriers. Another method for transformation employs polyethylene glycol/DMSO, as described in Chung and Miller, *Nucleic Acids Res.*, 16: 3580 (1988). Yet another method is the use of the technique termed electroporation.

Bacterial cells used to produce the heterologous polypeptide of interest described in this invention are cultured in suitable media in which the promoters can be induced as described generally, e.g., in Sambrook et al., supra.

Any other necessary supplements besides carbon, nitrogen, and inorganic phosphate sources may also be included at appropriate concentrations, introduced alone or as a mixture with another supplement or medium such as a complex nitrogen source. The pH of the medium may be any pH from about 5–9, depending mainly on the host organism.

For induction, typically the cells are cultured until a certain optical density is achieved, e.g., a $A_{550}$ of about 80–100, at which point induction is initiated (e.g., by addition of an inducer, by depletion of a repressor, suppressor, or medium component, etc.), to induce expression of the gene encoding the heterologous polypeptide. When about 50% or more of the heterologous polypeptide has accumulated (as determined, e.g., by the optical density reaching a target amount observed in the past to correlate with the desired heterologous polypeptide accumulation, e.g., a $A_{550}$ of about 120–140), induction of the promoter is effected for the lysis enzymes. The induction typically takes place at a point in time post-inoculation about 75–90%, preferably about 80–90%, of the total fermentation process time, as determined from prior experience and assays. For example, induction of the promoter may take place at from about 30 hours, preferably 32 hours, up to about 36 hours post-inoculation of a 40-hour fermentation process.

Gene expression may be measured in a sample directly, for example, by conventional northern blotting to quantitate the transcription of mRNA (Thomas, *Proc. Natl. Acad. Sci. USA*, 77: 5201–5205 (1980)). Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like.

For accumulation of an expressed gene product, the host cell is cultured under conditions sufficient for accumulation of the gene product. Such conditions include, e.g., temperature, nutrient, and cell-density conditions that permit protein expression and accumulation by the cell. Moreover, such conditions are those under which the cell can perform basic cellular functions of transcription, translation, and passage of proteins from one cellular compartment to another for the secreted proteins, as are known to those skilled in the art.

After product accumulation, when the cells have been lysed by the lytic enzymes expressed, optionally before product recovery the broth lysate is incubated for a period of time sufficient to release the heterologous polypeptide contained in the cells. This period of time will depend, for example, on the type of heterologous polypeptide being recovered and the temperature involved, but preferably will range from about 1 to 24 hours, more preferably 2 to 24 hours, and most preferably 2 to 3 hours. If there is overdigestion with the enzyme, the improvement in recovery of product will not be as great.

In the second step of this invention, the heterologous polypeptide, as a soluble or insoluble product released from the cellular matrix, is recovered from the lysate, in a manner that minimizes co-recovery of cellular debris with the product. The recovery may be done by any means, but preferably comprises sedimenting refractile particles containing the heterologous polypeptide or collecting supernatant containing soluble product. An example of sedimentation is centrifugation. In this case, the recovery preferably takes place, before EBA or sedimentation, in the presence of an agent that disrupts the outer cell wall to increase permeability and allows more solids to be recovered. Examples of such agents include a chelating agent such as EDTA or a zwitterion such as, for example, a dipolar ionic detergent such as ZWITTERGENT 316™ detergent. See Stabel et al., supra. Most preferably, the recovery takes place in the presence of EDTA. Another technique for the recovery of soluble product is EBA, as described above.

If centrifugation is used for recovery, the relative centrifugal force (RCF) is an important factor. The RCF is adjusted to minimize co-sedimentation of cellular debris with the refractile particles released from the cell wall at lysis. The specific RCF used for this purpose will vary with, for example, the type of product to be recovered, but preferably is at least about 3000×g, more preferably about 3500–6000×g, and most preferably about 4000–6000×g. For the case with t-gene co-expression, about 6000 rpm provides as good a recovery of refractile particles from lysed broth as for intact cells.

The duration of centrifugation will depend on several factors. The sedimentation rate will depend upon, e.g., the size, shape, and density of the retractile particle and the density and viscosity of the fluid. The sedimentation time for solids will depend, e.g., on the sedimentation distance and rate. It is reasonable to expect that the continuous disc-stack centrifuges would work well for the recovery of the released heterologous polypeptide aggregates or for the removal of cellular debris at large scale, since these centrifuges can process at high fluid velocities because of their relatively large centrifugal force and the relatively small sedimentation distance.

The heterologous polypeptide captured in the initial recovery step may then be further purified from the contaminating protein. In a preferred embodiment, the aggregated heterologous polypeptide is isolated, followed by a simultaneous solubilization and refolding of the polypeptide, as disclosed in U.S. Pat. No. 5,288,931. Alternatively, the soluble product is recovered by standard techniques.

The following procedures are exemplary of suitable purification procedures for the soluble heterologous polypeptide released from the periplasm or the cytoplasm: fractionation on immunoaffinity or ion-exchange columns; ethanol precipitation; reverse-phase HPLC; chromatography on silica or on a cation-exchange resin such as DEAE; chromatofocusing; SDS-PAGE; ammonium sulfate precipitation; and gel filtration using, for example, SEPHADEX™ G-75.

The following examples are offered by way of illustration and not by way of limitation. The disclosures of all patent and scientific references cited in the specification are expressly incorporated herein by reference.

EXAMPLE I

Co-expression of Lytic Enzymes with Soluble Product

A. Co-expression with T4-lysozyme and endA Endonuclease:

Background:

rhuMAb CD18 is a recombinant F(ab') antibody fragment with two 214-residue light chains and two 241-residue heavy chains. It binds to the MAC-1 (CD11b/CD18) receptor, effectively blocking the binding of neutrophils to the endothelium. In the fermentation process described below, rhuMab CD18 is produced as a $F(ab')_2$-leucine zipper precursor in *E. coli* and secreted into the periplasm. The desired recovery process targets the soluble fraction of the accumulated product and depends on the $F(ab')_2$-leucine zipper being released from the periplasm for initial capture.

T4-lysozyme co-expression was introduced to weaken the peptidoglycan sacculus, and the over-expression of endA protein was introduced to degrade genomic DNA released from the cells under conditions such that the cells are permeabilized or lysed.

In *E. coli*, the gene endA encodes for an endonuclease normally secreted to the periplasm that cleaves DNA into oligodeoxyribonucleotides in an endonucleolytic manner. It has been suggested that endA is relatively weakly expressed by *E. coli* (Wackernagel et al., supra). However, one could over-express the endonuclease with the use of a compatible plasmid. By inserting the enda gene with its signal sequence behind the ara-T4-lysozyme cassette in the compatible plasmid pJJ153, now pJJ154, expression of both T4-lysozyme and endonuclease will be induced upon addition of arabinose. While T4-lysozyme is locked inside the cytoplasm, endonuclease is secreted into the periplasmic space and kept away from the genomic DNA located in the cytoplasm during the fermentation process. An effective enzymatic degradation of DNA upon cell lysis is expected to reduce or even eliminate multiple passes through the mechanical disruption device, an operation often needed for both cell disruption and viscosity reduction. Success in doing so would bring significant time and cost reduction to the recovery process.

Materials and Methods:

pS1130 Plasmid Construction: Plasmid pS1130 (FIG. 3) was constructed to direct the production of the rhuMAb CD18 F(ab')$_2$-leucine zipper precursor in *E. coli*. It is based on the well-characterized plasmid pBR322 with a 2138-bp expression cassette (FIG. 4; SEQ ID NOS:1, 2 and 3) inserted into the EcoRI restriction site. The plasmid encodes for resistance to both tetracycline and beta-lactam antibiotics. The expression cassette contains a single copy of each gene linked in tandem. Transcription of each gene into a single dicistronic mRNA is directed by the *E. coli* phoA promoter (Chang et al., *Gene*, 44: 121–125 (1986)) and ends at the phage lambda $t_o$ terminator (Scholtissek and Grosse, *Nuc. Acids Res.*, 15: 3185 (1987)). Translation initiation signals for each chain are provided by *E. coli* STII (heat-stable enterotoxin) (Picken et al., *Infection and Immunity*, 42: 269–275 (1983)) Shine-Dalgarno sequences.

rhuMAb CD18 was created by humanization of the murine monoclonal antibody muMAb H52 (Hildreth and August, *J. Immunology*, 134: 3272–3280 (1985)) using a process previously described for other antibodies (Carter et al., *Proc. Natl. Acad. Sci. USA*, 89: 4285–4289 (1992); Shalaby et al., *J. Exp. Med.*, 175: 217–225 (1992); Presta et al., *J. Immunol.*, 151: 2623–2632 (1993)). Briefly, cDNAs encoding the muMAb H52 variable light ($V_L$) and variable heavy ($V_H$) chain domains were isolated using RT-PCR from a hybridoma cell line licensed from Hildreth (Hildreth and August, supra). The complementarity-determining regions (CDRs) of the muMAb H52 were transplanted into the human antibody framework gene encoding huMAb UCHT1-1 (Shalaby et al., supra) by site-directed mutagenesis. Non-CDR, murine framework residues that might influence the affinity of the humanized antibody for its target, human CD18, were identified using molecular modeling. These residues were altered by site-directed mutagenesis and their influence on CD18 binding was tested. Those framework residues that significantly improved affinity were incorporated into the humanized antibody. The expression vector encoding the final humanized version of muMAb H52 in an Fab' format was named pH52-10.0 and it is a derivative of pAK19 (Carter et al., *Bio/Technology*, 10: 163–167 (1992)).

Plasmid pS1130 differs from pH52-10.0 in the heavy-chain coding region. The C-terminus of the heavy chain was extended from CysProPro to the natural hinge sequence CysProProCysProAlaProLeuLeuGlyGly (SEQ ID NO:4) and then fused to the 33-residue leucine zipper domain of the yeast transcription factor GCN4. As described above, the leucine zipper domains dimerize to bring two Fab' molecules together and drive F(ab')$_2$ complex formation. The two cysteine residues in the heavy-chain hinge region then disulfide bond to those from an adjacent Fab' to form a covalently-linked F(ab')$_2$.

Plasmid pS1130 was constructed in a multi-step process outlined below:

First, a filamentous phage (f1) origin of replication was introduced into pH52-10.0 to create plasmid pSO858. Plasmid pSO858 was constructed by ligating the 1977-bp HindIII-HindIII fragment, containing the Fab' expression cassette of pH52–10.0, with the 4870-bp HindIII-HindIII fragment of plasmid pSO191 (referred to as phGHr (1-238) in Fuh et al., *J. Biol. Chem.*, 265: 3111–3115 (1990)).

Second, oligonucleotide-directed mutagenesis was performed on pSO858 to create plasmid zpil#6. The heavy-chain coding region was extended to include the 2-hinge cysteine residues and pepsin cleavage site: (CysProProCysProAlaProLeuLeuGlyGly; SEQ ID NO:4). A NotI restriction site was also introduced. The sequence of the introduced DNA was confirmed by DNA sequencing.

Third, a DNA fragment encoding the GCN4 leucine zipper domain flanked by NotI and SphI restriction sites was generated (WO98/37200 published Aug. 27, 1998). This 107-bp NotI-SphI DNA fragment was subsequently cloned into similarly-cut zipl#6 to create plasmid pS1111.

Fourth, DNA sequencing of the GCN4 leucine zipper fragment revealed an error in the coding sequence. This error was corrected by oligonucleotide-directed mutagenesis and confirmed by DNA sequencing. The resulting correct plasmid was named pS1117.

The final step in the construction of pS1130 was to restore the tetracycline-resistance gene and remove the f1 origin from pS1117. This was accomplished by ligating the 2884-bp PstI-SphI fragment of pS1117 containing the Fab'-zipper expression cassette with the 3615-bp PstI-SphI fragment of pH52-10.0.

pJJ154 Plasmid Construction: Plasmid pJJ154 (FIG. 5) is a pACYC177 derivative that is compatible with pBR322 vectors. To construct pJJ154, pJJ153 as described below was digested with MluI and the vector fragment was ligated with PCR-amplified endA gene designed to encode MluI ends. The correct orientation of the plasmid was screened for by restriction digest to produce pJJ154.

The construction of pJJ153 (a pACYC177 derivative that is compatible with pBR322 vectors) is shown in FIG. 5. The ClaI/AlwNI fragment from pBR322 was inserted into ClaI/AlwNI-digested pBAD18 (Guzman et al., supra) to produce pJJ70. One round of site-directed mutagenesis was then performed, changing HindIII to StuI to obtain pJJ75. A second round of site-directed mutagenesis was done to change MluI to SacII, to produce pJJ76. Then XbaI/HindIII fragments from pJJ76 and from pBKIGF2B were ligated, and XbaI/HindIII fragments from this ligation product and from a T4 lysozyme/tac plasmid were ligated to produce pT4LysAra. Then BamHI (filled in)/ScaI-digested pACYC177 was ligated with ClaI/HindIII (both ends filled in)-digested pT4LysAra to produce pJJ153. The maps for pACYC177, pT4LysAra, and pJJ153 are shown in FIG. 5.

Bacterial Strains and Growth Conditions: Strain 33B8 (*E. coli* W3110 tonA phoA Δ(argF-lac) 189 deoC degP ilvG+ (kanS)) was used as the production host for the co-expression of T4-lysozyme and DNA-digesting protein from plasmid pJJ154 and the expression of rhuMAb CD18 F(ab')$_2$-leucine zipper from plasmid pS1130. Competent cells of 33B8 were co-transformed with pJJ154 and pSl130 using standard procedures. Transformants were picked from LB plates containing 20 ug/ml tetracycline and 50 ug/ml kanamycin (LB+Tet20+Kan50), streak-purified, and grown in LB broth with 20 ug/ml tetracycline and 50 ug/ml kanamycin in a 37° C. or 30° C. shaker/incubator before being stored in DMSO at −80° C.

For control runs, the host 33B8 was transformed with pS1130 and pJJ96 (analogous to pJJ154 except no nucleic acids encoding the T4-lysozyme and endA product were inserted into the vector) and isolated from similar selective medium.

rhuMAb CD18 F(ab')$_2$-Leucine Zipper Fermentation Process: A shake flask inoculum was prepared by inoculating sterile medium using a freshly thawed stock culture vial. Appropriate antibiotics were included in the medium to provide selective pressure to ensure retention of the plasmid. The shake flask medium composition is given in Table 1. Shake flasks were incubated with shaking at about 30° C. (28° C.–32° C.) for 14–18 hours. This culture was then used to inoculate the production fermentation vessel. The inoculation volume was between 0.1% and 10% of the initial volume of medium.

The production of the F(ab')$_2$-zipper precursor of rhuMAb CD18 was carried out in the production medium given in Table 2. The fermentation process was carried out at about 30° C. (28–32° C.) and about pH 7.0 (6.5–7.9). The aeration rate and the agitation rate were set to provide adequate transfer of oxygen to the culture. Production of the F(ab')$_2$-zipper precursor of rhuMAb CD18 occurred when the phosphate in the medium was depleted, typically 36–60 hours after inoculation.

TABLE 1

Shake Flask Medium Composition

| Ingredient | Quantity/ Liter |
|---|---|
| Tetracycline | 4–20 mg |
| Tryptone | 8–12 g |
| Yeast extract | 4–6 g |
| Sodium chloride | 8–12 g |
| Sodium phosphate, added as pH7 solution | 4–6 mmol |

TABLE 2

Production Medium Composition

| Ingredient | Quantity/ Liter |
|---|---|
| Tetracycline | 4–20 mg |
| Glucose[a] | 10–250 g |
| Ammonium sulfate[a] | 2–8 g |
| Sodium phosphate, monobasic, dihydrate[a] | 1–5 g |
| Potassium phosphate, dibasic[a] | 1–5 g |
| Potassium phosphate, monobasic[a] | 0.5–5 g |
| Sodium citrate, dihydrate[a] | 0.5–5 g |
| Magnesium sulfate, heptahydrate[a] | 1.0–10 g |
| FERMAX ™[a] (antifoam) | 0–5 ml |
| Ferric chloride, hexahydrate[a] | 20–200 mg |
| Zinc sulfate, heptahydrate[a] | 0.2–20 mg |
| Cobalt chloride, hexahydrate[a] | 0.2–20 mg |
| Sodium molybdate, dihydrate[a] | 0.2–20 mg |
| Cupric sulfate, pentahydrate[a] | 0.2–20 mg |
| Boric acid[a] | 0.2–20 mg |
| Manganese sulfate, monohydrate[a] | 0.2–20 mg |
| Casein digest | 15–25 g |
| Methionine[a] | 0–5 g |
| Leucine[a] | 0–5 g |

[a]A portion of these ingredients was added to the fermentor initially, and the remainder was fed during the fermentation. Ammonium hydroxide was added as required to control pH.

The timing of arabinose addition ranged from 50 to 65 hours post-inoculation. Bolus additions of 0.1% to 1% (final concentration) arabinose were tested for the induction of co-expression of T4-lysozyme and endA endonuclease.

The fermentation was allowed to proceed for about 65 hours (60 to 72 hours), after which the broth was harvested for subsequent treatment for product recovery.

Assessment of Reduction of Broth Viscosity by endA Endonuclease Over-Expression: Aliquots of harvested broth from the rhuMAb CD18 F(ab')$_2$-leucine zipper fermentation with or without the co-expression of endA product in addition to phage lysozyme described above was subjected to one cycle of freeze-thaw. The thawed broth was diluted 1:3 into water or 20 mM $MgCl_2$ before incubation in a 37° C. water bath with agitation. Samples were removed at intervals and the viscosity of the diluted broth was measured by using the Falling Ball viscometer.

Results:

Effect of Over-Expression of EndA in Addition to T4-Lysozyme on Broth Viscosity: As shown in Table 3, diluted freeze-thawed harvest broth from the above fermentation process in the absence of endA over-expression had broth viscosity in excess of 800 cP at the start of the 37° C. incubation. After 60 minutes of incubation, there was little change in the $H_2O$-diluted freeze-thawed fermentation broth viscosity, while the $MgCl_2$-buffer-diluted broth showed significant reduction in the broth viscosity. Upon extended 37° C. incubation for up to over 2.5 hours, the viscosity of the freeze-thawed diluted harvest broth with no over-expression of endA in addition to T4-lysozyme leveled off at about 40 cP. The viscosity of the diluted freeze-thawed harvest broth with over-expression of endA was less than 20 cP even before any 37° C. incubation.

TABLE 3

| Co-expression | Treatment | 37° C. Incubation (min) | Broth Viscosity (cP) |
|---|---|---|---|
| T4-lysozyme + endA (pJJ154) | $H_2O$ control | 0 | <20 |
| | + 20 mM $MgCl_2$ | 0 | <20 |
| | $H_2O$ control | 60 | <20 |
| | + 20 mM $MgCl_2$ | 60 | <20 |
| T4-lysozyme only (pJJ153) | $H_2O$ control | 0 | >800 |
| | + 20 mM $MgCl_2$ | 0 | >800 |
| | $H_2O$ control | 60 | >800 |
| | + 20 mM $MgCl_2$ | 60 | 36 |
| | $H_2O$ control | 120 | 41 |
| | + 20 mM $MgCl_2$ | 120 | 36 |
| | $H_2O$ control | 165 | 40 |
| | + 20 mM $MgCl_2$ | 165 | 42 |

B. Co-expression of T4-Lysozyme, Gene t, and EndA Endonuclease:

Background:

As described in Example IA, over-expression of endA brings significant benefit in lowering the viscosity of permeabilized or lysed broth. It helps in conditioning the fermentation broth for the subsequent product recovery step. By co-expressing T4-lysozyme and t-gene in addition to endA, cells can be biochemically lysed and at the same time yield a well-conditioned broth lysate with fluid viscosity sufficiently low and compatible with product isolation steps such as centrifugation or EBA.

The fermentation process described above was used to produce rhuMAb CD18 as a F(ab')$_2$-leucine zipper precursor directed by plasmid pS1130 in *E. coli*, with the co-expression of lytic enzymes and DNA-digesting protein directed by the plasmid pJJ155. in *E. coli*. The antibody fragment product was secreted and accumulated in the periplasm. The lytic enzymes were compartmentalized away from their substrate until released by the action of the t-gene product. The desired recovery process targets the soluble fraction of the F(ab')$_2$-leucine zipper released from the periplasm for initial capture.

Materials & Methods:

PJJ155 Plasmid Construction: Like pJJ154, pJJ155 is a pACYC177 derivative that is compatible with pBR322 vectors. To construct pJJ155, pJJ154 as described above was digested with KpnI and the vector fragment was ligated with PCR-amplified t-gene designed to encode KpnI ends. The correct orientation of the plasmid was screened for by restriction digest to product pJJ155. A map for pJJ155 is shown in FIG. 7.

Bacterial Strains and Growth Conditions: Most experiments were carried out with transformed 33B8 as described above except that pJJ154 was replaced by pJJ155.

Fermentation Process Description: See Example IA.

Results:

Cell growth of 33B8 co-transformed with pS1130 and pJJ155 (33B8/pS1130/pJJ155) was not significantly different from that of the control (33B8 transformed with pSl130 only). After addition of 0.5% to 1% arabinose at 50–65 hours to induce the co-expression of the lytic enzymes and DNA-digesting protein, OD550 of the 33B8/pS1130/pJJ155 culture steadily dropped to 30–40% of peak cell density, suggesting cell lysis.

Table 4 shows the effect of co-expression of T4-lysozyme+ endA+ t-gene on the release of soluble anti-CD18 antibody fragment into the medium. The supernatant from centrifugation of the harvested broth lysate after incubation in the presence of 25 mM EDTA was assayed by ion-exchange HPLC chromatography for product quantitation. Greater than 80% of the soluble anti-CD18 antibody fragments was found in the supernatant fraction for the experimental condition where co-expression of lytic enzymes and DNA-digesting protein was induced, compared to less than 10% found for the control and the condition with no t-gene (pJJ154) or mechanical disruption.

TABLE 4

| Co-Expression | % of Total Product Released |
|---|---|
| None (control) | <10 |
| T4-Lysozyme + endA (pJJ154) | <10 |
| T4-Lysozyme + endA + t-gene (pJJ155) | >80 |

Conclusions:

Endonuclease degrades DNA and lowers broth viscosity. Over-expression of *E. coli* endogenous endonuclease in addition to T4-lysozyme reduces the need for mechanical cell disruption for the shearing of released DNA. The release of the phage lysozyme from the cytoplasmic compartment mediated by the expressed t-gene protein initiates the biochemical disruption process, resulting in cell lysis and the release of cellular contents including heterologous polypeptide, genomic DNA, and the DNA-digesting protein, which was trapped in either the periplasm or the cytoplasm up to this time. By holding the broth lysate for appropriate digestion of substrates by the lytic enzymes and DNA-digesting protein co-expressed, the broth viscosity and product release from cellular matrix were improved for better product recovery.

EXAMPLE II

Co-expression of Lytic Enzymes with IGF-I

Background:

IGF-I was selected as a heterologous polypeptide for evaluation of refractile particle recovery due to large-scale needs. Co-expression of lytic enzymes and DNA-digesting protein was used to improve the release of the IGF-I retractile particles from cell-wall structures in the absence of mechanical disruption.

Upon cell lysis, in addition to releasing T4-lysozyme from the cytoplasmic compartment, genomic DNA released from the cytoplasm would have contributed significant viscosity to the broth lysate fluid. Hence, the co-expression of an *E. coli* endonuclease together with lytic enzymes was useful in reducing fluid viscosity following cell lysis and improving product recovery during centrifugation.

Materials & Methods:

pLBIGF57 Plasmid Construction: The plasmid pLBIGF57 for the expression of IGF-I (FIG. 6) was constructed from a basic backbone of pBR322. The transcriptional and translational sequences required for the expression of nucleic acid encoding IGF-I were provided by the phoA promoter and trp Shine-Dalgarno sequence. Secretion of the protein was directed by a TIR variant of the lamB signal sequence. This TIR variant does not alter the primary amino acid sequence of the lamB signal; however, silent nucleotide sequence changes result, in this particular variant, in an increased level of translated protein.

The details of pLBIGF57 construction follow. A codon library of the lamB signal sequence was constructed to screen for translational initiation region (TIR) variants of differing strength. Specifically, the third position of codons 3 to 7 of the lamB signal sequence was varied. This design conserved the wild-type amino acid sequence and yet allowed for divergence within the nucleotide sequence.

As previously described for the screening of the STII signal sequence codon library (S. African Pat. No. ZA 96/1688; Simmons and Yansura, *Nature Biotechnology*, 14: 629–634 (1996)), the phoa gene product served as a reporter for the selection of the lamB TIR variants. The codon library of the lamB signal sequence was inserted downstream of the phoA promoter and trp Shine-Dalgarno and upstream of the phoA gene. Under conditions of low transcriptional activity, the quantity of alkaline phosphatase secreted by each construct was now dependent on the efficiency of translational initiation provided by each TIR variant in the library. Using this method, lamB TIR variants were selected covering an approximate 10-fold activity range. Specifically, lamB TIR variant #57 provides an approximately 1.8-fold stronger TIR than the wild-type lamB codons based on the phoA activity assay.

The vector fragment for the construction of pLBIGF57 was generated by digesting pBK131Ran with XbaI and SphI. This XbaI-SphI vector contains the phoA promoter and trp Shine-Dalgarno sequences. The coding sequences for IGF-I and the lambda $t_o$ transcription terminator were isolated from pBKIGF-2B (U.S. Pat. No. 5,342,763) following digestion with NcoI-SphI. The lamB signal sequence fragment was isolated from pLBPhoTBK#57 (TIR variant #57; generated as described above) following digestion with XbaI-NcoI. These three fragments were then ligated together to construct pLBIGF57.

Bacterial Strains and Growth Conditions: Most experiments were carried out with strain 43E7 (*E. coli* W3110 fhuA (tonA) Δ(argF-lac) ptr3 degP41(kanS) ΔompTΔ(nmpc-fepE) ilvG+ phoA+). A double-plasmid system involving the product plasmid (pLBIGF57) and pJJ155 for the lytic enzymes was employed. Competent cells of 43E7 were co-transformed with pLBIGF57 and pJJ155 using the standard procedure. Transformants were picked after growth on an LB plate containing 50 $\mu$g/mL carbenicillin (LB+ CARB50™) and 50 $\mu$g/ml kanamycin, streak-purified and grown in LB broth with 50 $\mu$g/mL CARB50™ and 50 $\mu$g/ml kanamycin in a 37° C. shaker/incubator before being tested in the fermentor.

For comparison, 43E7 transformed with pLBIGF57 alone was used in the control case conducted under similar conditions. pLBIGF57 confers both carbenicillin and tetracycline resistance to the production host and allows 43E7/pLBIGF57 to grow in the presence of either antibiotic.

Fermentation Process: The fermentation medium composition and experimental protocol used for the co-expression of nucleic acid encoding IGF-I, enda, T4-lysozyme, and t-gene if used were similar to those of the scaled-down high-metabolic rate, high-yield 10-kiloliter IGF-I process. Briefly, a shake flask seed culture of 43E7/pLBIGF57 or 43E7/ pLBIGF57/pJJ155 was used to inoculate the rich production medium. The composition of the medium (with the quantities of each component utilized per liter of initial medium) is described below:

| Ingredient | Quantity/L |
|---|---|
| Glucose* | 200–500 g |
| Ammonium Sulfate | 2–10 g |
| Sodium Phosphate, Monobasic Dihydrate | 1–5 g |
| Potassium Phosphate, Dibasic | 1–5 g |
| Sodium Citrate, Dihydrate | 0.5–5 g |
| Potassium Chloride | 0.5–5 g |
| Magnesium Sulfate, Heptahydrate | 0.5–5 g |
| PLURONIC ™ Polyol, L61 | 0.1–5 mL |
| Ferric Chloride, Heptahydrate | 10–100 mg |
| Zinc Sulfate, Heptahydrate | 0.1–10 mg |
| Cobalt Chloride, Hexahydrate | 0.1–10 mg |
| Sodium Molybdate, Dihydrate | 0.1–10 mg |
| Cupric Sulfate, Pentahydrate | 0.1–10 mg |
| Boric Acid | 0.1–10 mg |
| Manganese Sulfate, Monohydrate | 0.1–10 mg |
| Hydrochloric Acid | 10–100 mg |
| Tetracycline | 4–30 mg |
| Yeast Extract* | 5–25 g |
| NZ Amine AS* | 5–25 g |
| Methionine* | 0–5 g |
| Ammonium Hydroxide | as required to control pH |
| Sulfuric Acid | as required to control pH |

*A portion of the glucose, yeast extract, NZ Amine AS, and methionine is added to the medium initially, with the remainder being fed throughout the fermentation.

The fermentation was a fed-batch process with fermentation parameters set as follow:

| | |
|---|---|
| Agitation: | Initially at 800 RPM, increased to 1000 RPM at 8 OD |
| Aeration: | 15.0 slpm |
| pH control: | 7.3 |
| Temp.: | 37° C. |
| Back pressure: | 0.7 bar |
| Glucose feed: | computer-controlled using an algorithm which regulates the growth rate at approximately 95% of the maximum early in the fermentation and which then controls the dissolved oxygen concentration ($DO_2$) at 30% of air saturation after the $DO_2$ drops to 30%. |
| Complex nitrogen feed: | constant feed rate of 0.5 mL/min throughout the run |
| Run Duration: | 40 hours |

The timing of arabinose addition ranged from 24 hr to 36 hr. Bolus additions of 0.1% to 1% (final concentration) arabinose were tested to define the induction strength necessary for producing the most preferred amounts of T4-lysozyme for better product recovery at the centrifugation step.

Recovery of Refractile Particles from Harvested Broth:

Broth was harvested at the end of fermentation when a target drop in $OD_{550}$ was observed and was either processed soon after or stored briefly at 4° C. prior to use. The test protocol used involved four process steps:

I. Add 1M EDTA to the harvest broth to bring the final concentration of EDTA to 25 mM. EDTA chelates the divalent cations and disrupts the outer cell surface structure. This makes the peptidoglycan layer inside unbroken cells accessible to degradation by T4-lysozyme and weakens the cell wall to promote cell lysis.

II. Hold the lysate at room temperature or incubate at 37° C. for further degradation of cell wall. This step simulates the longer process times associated with the larger-scale process.

III. Recover retractile particles and solids from the lysate by centrifugation. Bench-scale centrifugation in a SORVALL™ GSA rotor at different speeds (3000 rpm to 6000 rpm; equivalent to RCF's of approximately 2500 g to 6000 g at rmax, respectively) was used to collect the solids as pellets.

An additional step to wash the pellet with buffer would remove the lysate entrained by the pellet and minimize the amount of contaminating *E. coli* proteins in the retractile particle preparations.

Samples of the supernatant and pellet from centrifugation of broth lysate resuspended in buffer were evaluated for product recovery. The amount of product present in the samples was analyzed by a HPLC reverse-phase method. Product recovery efficiency was calculated by expressing the amount of product recovered in the pellet by the process step as a percent of the total product present in the pellet and supernatant combined. To evaluate the quality of the refractile particles recovered, the amount of total protein present in the pellet and the supernatant was measured by the Lowry method (*J. Biol. Chem*., 193: 265 (1951)).

The contribution of endonuclease activity was assessed by the efficiency of solids recovery during sedimentation from the broth lysate by centrifugation. Also, the amount of nucleic acids present in the pellet and the supernatant was measured by $OD_{260}$ readings.

Results:

IGF-I Fermentation and Product Expression:

FIG. 8 shows in general the two-plasmid system employed in this Example for co-expression of lytic enzymes and enda with IGF-I using pJJ155. The initial growth rate of 43E7/pLBIGF57/pJJ155 showed no significant difference from that of the 43E7/pLBIGF57 control. Peak cell densities reached in these broths were similar. However, compared to the control, a significant loss in optical density was observed in cultures after induction for lytic enzyme co-expression, indicating cell lysis. Examination of the harvest broth by phase-contrast microscopy showed that, in comparison to the no-co-expression control, very few intact *E. coli* cells were present and freed retractile particles were evident as a result of the co-expression of lytic enzymes and DNA-digesting protein. See FIGS. 9A–9E.

The respiration rates across this collection of runs looked very similar to the control except for significant continuous loss in oxygen uptake rate (OUR) with a concomitant loss in kla soon after the arabinose addition.

The success of the biochemical cell lysis technique as described in this invention is evident from the differences in the partitioning of nucleic acids and total protein between the solid (pellet) and liquid (supernatant) fractions as a result of the co-expression of the lytic enzymes and DNA-digesting protein versus the control with no co-expression (FIGS. 10A and 10B, respectively). The percent of total nucleic acids calculated from A260 readings and the percent of total protein as measured by the Lowry protein assay both increased in the supernatant from the centrifugation of biochemically lysed broth over that from control broth.

The product recovery from the two conditions is summarized in FIG. 11. With the biochemically-lysed IGF-I broth, IGF-I product was released together with degraded DNA polymer into the broth lysate. The efficiency of recovering the small dense retractile particles increased with the RCF used during centrifugation. As higher g force was used, the percent of the lysed broth recovered as pellet (reported as % pellet) increased (FIG. 12), and so did the amount of IGF-I product in the pellet. At approximately 6000×g, close to 95% of the product was captured in the pellet.

Conclusion:

As disclosed herein, a simple manipulation of gene expression during the fermentation process resulted in a biochemical cell lysis that could replace the conventional mechanical disruption traditionally used for product recovery at production scale. In vivo co-expression or coordinated expression of T4-lysozyme and t-gene product is a highly effective technique for the disintegration of cells while the over-expressed enda protein degrades the leaked DNA, lowers broth viscosity, and efficiently conditions the broth lysate for product recovery in the initial product capture step. Biochemical cell lysis is applicable to the recovery of soluble as well as insoluble product. The compartmentalization of the co-expressed enzymes away from their substrates until the desired moment for cell lysis is essential and a critical design in the invention. The invention brings significant reduction in process cost, process time, and hence opportunity cost to other products that may be sharing the same production facility.

What is claimed is:

1. A process for recovering a heterologous polypeptide from bacterial cells comprising:

(a) culturing the cells which comprise a first nucleic acid encoding phage lysozyme and a second nucleic acid encoding a protein that displays DNA-digesting activity under the control of a signal sequence for secretion of the DNA-digesting protein, wherein said first and second nucleic acids are operatively linked to a first promoter that is the same for both and wherein both are linked on the same nucleic acid construct, and a third nucleic acid encoding the heterologous polypeptide and a signal sequence for secretion of the heterologous polypeptide, which third nucleic acid is linked to a second promoter, wherein the second promoter is inducible and the first promoter is different from the second promoter and is either (i) inducible or (ii) a weak constitutive promoter that does not require the addition of an inducer to function as a promoter, (b) adding an inducer specific for induction of expression of the nucleic acid encoding the heterologous polypeptide from the second, inducible promoter, (c) optionally, when the first promoter driving expression of the nucleic acids encoding the DNA-digesting protein and the phage lysozyme is an inducible promoter, adding an inducer specific for the first promoter after accumulation of about 50% or more of the maximum accumulation of the heterologous polypeptide to be recovered, (d) lysing the cells, and (e) recovering accumulated heterologous polypeptide from the broth lysate.

2. The process of claim 1 wherein the heterologous polypeptide is a mammalian polypeptide.

3. The process of claim 2 wherein the heterologous polypeptide is anti-CD18 antibody or an anti-CD18 antibody fragment.

4. The process of claim 1 wherein the recovery step is performed using expanded bed absorption or sedimentation.

5. The process of claim 1 wherein the DNA-digesting protein is a eukaryotic DNase or bacterial endA.

6. The process of claim 1 wherein the bacterial cells are gram-negative cells.

7. The process of claim 1 wherein the phage lysozyme is phage T4 lysozyme.

8. The process of claim 1 wherein the cell lysis takes place in the presence of an agent that disrupts the outer cell wall of the bacterial cells.

9. The process of claim 8 wherein the agent is a chelating agent or zwitterion.

10. The process of claim 1 wherein, before recovery, the cell lysate is incubated for a period of time sufficient to release the heterologous polypeptide contained in the cells.

11. The process of claim 1 wherein one or more of the nucleic acids, including the promoter therefor, is integrated into the genome of the bacterial cells.

12. The process of claim 1 wherein the culturing takes place under conditions whereby the heterologous polypeptide and DNA-digesting protein are secreted into the periplasm of the bacteria.

* * * * *

SEQUENCE LISTING

```
<160> NUMBER OF SEQ ID NOS:  4

<210> SEQ ID NO 1
<211> LENGTH: 6550
<212> TYPE: DNA
<213> ORGANISM: Human

<400> SEQUENCE: 1

gaattcaact tctccatact ttggataagg aaatacagac atgaaaaatc          50

tcattgctga gttgttattt aagcttgccc aaaaagaaga agagtcgaat         100

gaactgtgtg cgcaggtaga agctttggag attatcgtca ctgcaatgct         150

tcgcaatatg gcgcaaaatg accaacagcg gttgattgat caggtagagg         200

gggcgctgta cgaggtaaag cccgatgcca gcattcctga cgacgatacg         250

gagctgctgc gcgattacgt aaagaagtta ttgaagcatc ctcgtcagta         300

aaaagttaat cttttcaaca gctgtcataa agttgtcacg gccgagactt         350

atagtcgctt tgtttttatt ttttaatgta tttgtaacta gaattcgagc         400

tcgccgggga tcctctagag gttgaggtga ttttatgaaa aagaatatcg         450

catttcttct tgcatctatg ttcgtttttt ctattgctac aaacgcgtac         500

gctgatatcc agatgaccca gtccccgagc tccctgtccg cctctgtggg         550

cgatagggtc accatcacct gtcgtgccag tcaggacatc aacaattatc         600

tgaactggta tcaacagaaa ccaggaaaag ctccgaaact actgatttac         650

tatacctcca ccctccactc tggagtccct tctcgcttct ctggttctgg         700

ttctgggacg gattacactc tgaccatcag cagtctgcaa ccggaggact         750

tcgcaactta ttactgtcag caaggtaata ctctgccgcc gacgttcgga         800

cagggcacga aggtggagat caaacgaact gtggctgcac catctgtctt         850

catcttcccg ccatctgatg agcagttgaa atctggaact gcctctgttg         900

tgtgcctgct gaataacttc tatcccagag aggccaaagt acagtggaag         950

gtggataacg ccctccaatc gggtaactcc caggagagtg tcacagagca        1000

ggacagcaag gacagcacct acagcctcag cagcaccctg acgctgagca        1050

aagcagacta cgagaaacac aaagtctacg cctgcgaagt cacccatcag        1100

ggcctgagct cgcccgtcac aaagagcttc aacaggggag agtgttaagc        1150

tgatcctcta cgccggacgc atcgtggcgc tagtacgcaa gttcacgtaa        1200

aaacggtatc tagaggttga ggtgatttta tgaaaaagaa tatcgcattt        1250

cttcttgcat ctatgttcgt tttttctatt gctacaaacg cgtacgctga        1300
```

-continued

```
ggttcagctg gtggagtctg gcggtggcct ggtgcagcca gggggctcac          1350
tccgtttgtc ctgtgcaact tctggctaca cctttaccga atacactatg          1400
cactggatgc gtcaggcccc gggtaagggc ctggaatggg ttgcagggat          1450
taatcctaaa aacggtggta ccagccacaa ccagaggttc atggaccgtt          1500
tcactataag cgtagataaa tccaccagta cagcctacat gcaaatgaac          1550
agcctgcgtg ctgaggacac tgccgtctat tattgtgcta gatggcgagg          1600
cctgaactac ggctttgacg tccgttattt tgacgtctgg ggtcaaggaa          1650
ccctggtcac cgtctcctcg gcctccacca agggcccatc ggtcttcccc          1700
ctggcaccct cctccaagag cacctctggg ggcacagcgg ccctgggctg          1750
cctggtcaag gactacttcc ccgaaccggt gacggtgtcg tggaactcag          1800
gcgccctgac cagcggcgtg cacaccttcc cggctgtcct acagtcctca          1850
ggactctact ccctcagcag cgtggtgacc gtgccctcca gcagcttggg          1900
cacccagacc tacatctgca acgtgaatca caagcccagc aacaccaagg          1950
tcgacaagaa agttgagccc aaatcttgtg acaaaactca cacatgcccg          2000
ccgtgcccag caccagaact gctgggcggc cgcatgaaac agctagagga          2050
caaggtcgaa gagctactct ccaagaacta ccacctagag aatgaagtgg          2100
caagactcaa aagcttgtc ggggagcgct aagcatgcga cggccctaga          2150
gtccctaacg ctcggttgcc gccgggcgtt ttttattgtt aactcatgtt          2200
tgacagctta tcatcgataa gctttaatgc ggtagtttat cacagttaaa          2250
ttgctaacgc agtcaggcac cgtgtatgaa atctaacaat gcgctcatcg          2300
tcatcctcgg caccgtcacc ctggatgctg taggcatagg cttggttatg          2350
ccggtactgc cgggcctctt gcgggatatc gtccattccg acagcatcgc          2400
cagtcactat ggcgtgctgc tagcgctata tgcgttgatg caatttctat          2450
gcgcacccgt tctcggagca ctgtccgacc gctttggccg ccgcccagtc          2500
ctgctcgctt cgctacttgg agccactatc gactacgcga tcatggcgac          2550
cacacccgtc ctgtggatcc tctacgccgg acgcatcgtg gccggcatca          2600
ccggcgccac aggtgcggtt gctggcgcct atatcgccga catcaccgat          2650
ggggaagatc gggctcgcca cttcgggctc atgagcgctt gtttcggcgt          2700
gggtatggtg gcaggccccg tggccggggg actgttgggc gccatctcct          2750
tgcacgcacc attccttgcg gcggcggtgc tcaacggcct caacctacta          2800
ctgggctgct tcctaatgca ggagtcgcat aagggagagc gtcgtccgat          2850
gcccttgaga gccttcaacc cagtcagctc cttccggtgg gcgcggggca          2900
tgactatcgt cgccgcactt atgactgtct tctttatcat gcaactcgta          2950
ggacaggtgc cggcagcgct ctgggtcatt ttcggcgagg accgctttcg          3000
ctggagcgcg acgatgatcg gcctgtcgct tgcggtattc ggaatcttgc          3050
acgccctcgc tcaagccttc gtcactggtc ccgccaccaa acgtttcggc          3100
gagaagcagg ccattatcgc cggcatggcg gccgacgcgc tgggctacgt          3150
cttgctggcg ttcgcgacgc gaggctggat ggccttcccc attatgattc          3200
ttctcgcttc cggcggcatc gggatgcccg cgttgcaggc catgctgtcc          3250
```

-continued

```
aggcaggtag atgacgacca tcagggacag cttcaaggat cgctcgcggc      3300
tcttaccagc ctaacttcga tcactggacc gctgatcgtc acggcgattt      3350
atgccgcctc ggcgagcaca tggaacgggt tggcatggat tgtaggcgcc      3400
gccctatacc ttgtctgcct ccccgcgttg cgtcgcggtg catggagccg      3450
ggccacctcg acctgaatgg aagccggcgg cacctcgcta acggattcac      3500
cactccaaga attggagcca atcaattctt gcggagaact gtgaatgcgc      3550
aaaccaaccc ttggcagaac atatccatcg cgtccgccat ctccagcagc      3600
cgcacgcggc gcatctcggg cagcgttggg tcctggccac gggtgcgcat      3650
gatcgtgctc ctgtcgttga ggacccggct aggctggcgg ggttgcctta      3700
ctggttagca gaatgaatca ccgatacgcg agcgaacgtg aagcgactgc      3750
tgctgcaaaa cgtctgcgac ctgagcaaca acatgaatgg tcttcggttt      3800
ccgtgtttcg taaagtctgg aaacgcggaa gtcagcgccc tgcaccatta      3850
tgttccggat ctgcatcgca ggatgctgct ggctaccctg tggaacacct      3900
acatctgtat taacgaagcg ctggcattga ccctgagtga tttttctctg      3950
gtcccgccgc atccataccg ccagttgttt accctcacaa cgttccagta      4000
accgggcatg ttcatcatca gtaacccgta tcgtgagcat cctctctcgt      4050
ttcatcggta tcattacccc catgaacaga aattccccct tacacggagg      4100
catcaagtga ccaaacagga aaaaaccgcc cttaacatgg cccgctttat      4150
cagaagccag acattaacgc ttctggagaa actcaacgag ctggacgcgg      4200
atgaacaggc agacatctgt gaatcgcttc acgaccacgc tgatgagctt      4250
taccgcagct gcctcgcgcg tttcggtgat gacggtgaaa acctctgaca      4300
catgcagctc ccggagacgg tcacagcttg tctgtaagcg gatgccggga      4350
gcagacaagc ccgtcagggc gcgtcagcgg gtgttggcgg gtgtcggggc      4400
gcagccatga cccagtcacg tagcgatagc ggagtgtata ctggcttaac      4450
tatgcggcat cagagcagat tgtactgaga gtgcaccata tgcggtgtga      4500
aataccgcac agatgcgtaa ggagaaaata ccgcatcagg cgctcttccg      4550
cttcctcgct cactgactcg ctgcgctcgg tcgttcggct gcggcgagcg      4600
gtatcagctc actcaaaggc ggtaatacgg ttatccacag aatcagggga      4650
taacgcagga aagaacatgt gagcaaaagg ccagcaaaag gccaggaacc      4700
gtaaaaaggc cgcgttgctg gcgtttttcc ataggctccg cccccctgac      4750
gagcatcaca aaaatcgacg ctcaagtcag aggtggcgaa acccgacagg      4800
actataaaga taccaggcgt ttccccctgg aagctccctc gtgcgctctc      4850
ctgttccgac cctgccgctt accggatacc tgtccgcctt tctcccttcg      4900
ggaagcgtgg cgctttctca tagctcacgc tgtaggtatc tcagttcggt      4950
gtaggtcgtt cgctccaagc tgggctgtgt gcacgaaccc cccgttcagc      5000
ccgaccgctg cgccttatcc ggtaactatc gtcttgagtc caacccggta      5050
agacacgact tatcgccact ggcagcagcc actggtaaca ggattagcag      5100
agcgaggtat gtaggcggtg ctacagagtt cttgaagtgg tggcctaact      5150
acggctacac tagaaggaca gtatttggta tctgcgctct gctgaagcca      5200
gttaccttcg gaaaaagagt tggtagctct tgatccggca aacaaaccac      5250
```

-continued

```
cgctggtagc ggtggttttt ttgtttgcaa gcagcagatt acgcgcagaa 5300
aaaaaggatc tcaagaagat cctttgatct tttctacggg gtctgacgct 5350
cagtggaacg aaaactcacg ttaagggatt ttggtcatga gattatcaaa 5400
aaggatcttc acctagatcc ttttaaatta aaaatgaagt tttaaatcaa 5450
tctaaagtat atatgagtaa acttggtctg acagttacca atgcttaatc 5500
agtgaggcac ctatctcagc gatctgtcta tttcgttcat ccatagttgc 5550
ctgactcccc gtcgtgtaga taactacgat acgggagggc ttaccatctg 5600
gccccagtgc tgcaatgata ccgcgagacc cacgctcacc ggctccagat 5650
ttatcagcaa taaaccagcc agccggaagg gccgagcgca gaagtggtcc 5700
tgcaacttta tccgcctcca tccagtctat taattgttgc cgggaagcta 5750
gagtaagtag ttcgccagtt aatagtttgc gcaacgttgt tgccattgct 5800
gcaggcatcg tggtgtcacg ctcgtcgttt ggtatggctt cattcagctc 5850
cggttcccaa cgatcaaggc gagttacatg atcccccatg ttgtgcaaaa 5900
aagcggttag ctccttcggt cctccgatcg ttgtcagaag taagttggcc 5950
gcagtgttat cactcatggt tatggcagca ctgcataatt ctcttactgt 6000
catgccatcc gtaagatgct tttctgtgac tggtgagtac tcaaccaagt 6050
cattctgaga atagtgtatg cggcgaccga gttgctcttg cccggcgtca 6100
acacgggata ataccgcgcc acatagcaga actttaaaag tgctcatcat 6150
tggaaaacgt tcttcggggc gaaaactctc aaggatctta ccgctgttga 6200
gatccagttc gatgtaaccc actcgtgcac ccaactgatc ttcagcatct 6250
tttactttca ccagcgtttc tgggtgagca aaaacaggaa ggcaaaatgc 6300
cgcaaaaaag ggaataaggg cgacacggaa atgttgaata ctcatactct 6350
tcctttttca atattattga agcatttatc agggttattg tctcatgagc 6400
ggatacatat ttgaatgtat ttagaaaaat aaacaaatag gggttccgcg 6450
cacatttccc cgaaaagtgc cacctgacgt ctaagaaacc attattatca 6500
tgacattaac ctataaaaat aggcgtatca cgaggccctt tcgtcttcaa 6550
```

```
<210> SEQ ID NO 2
<211> LENGTH: 237
<212> TYPE: PRT
<213> ORGANISM: Human

<400> SEQUENCE: 2

Met Lys Lys Asn Ile Ala Phe Leu Leu Ala Ser Met Phe Val Phe
  1               5                  10                  15

Ser Ile Ala Thr Asn Ala Tyr Ala Asp Ile Gln Met Thr Gln Ser
                 20                  25                  30

Pro Ser Ser Leu Ser Ala Ser Val Gly Asp Arg Val Thr Ile Thr
                 35                  40                  45

Cys Arg Ala Ser Gln Asp Ile Asn Asn Tyr Leu Asn Trp Tyr Gln
                 50                  55                  60

Gln Lys Pro Gly Lys Ala Pro Lys Leu Leu Ile Tyr Tyr Thr Ser
                 65                  70                  75

Thr Leu His Ser Gly Val Pro Ser Arg Phe Ser Gly Ser Gly Ser
                 80                  85                  90
```

-continued

```
Gly Thr Asp Tyr Thr Leu Thr Ile Ser Ser Leu Gln Pro Glu Asp
                95                  100                 105

Phe Ala Thr Tyr Tyr Cys Gln Gln Gly Asn Thr Leu Pro Pro Thr
                110                 115                 120

Phe Gly Gln Gly Thr Lys Val Glu Ile Lys Arg Thr Val Ala Ala
                125                 130                 135

Pro Ser Val Phe Ile Phe Pro Pro Ser Asp Glu Gln Leu Lys Ser
                140                 145                 150

Gly Thr Ala Ser Val Val Cys Leu Leu Asn Asn Phe Tyr Pro Arg
                155                 160                 165

Glu Ala Lys Val Gln Trp Lys Val Asp Asn Ala Leu Gln Ser Gly
                170                 175                 180

Asn Ser Gln Glu Ser Val Thr Glu Gln Asp Ser Lys Asp Ser Thr
                185                 190                 195

Tyr Ser Leu Ser Ser Thr Leu Thr Leu Ser Lys Ala Asp Tyr Glu
                200                 205                 210

Lys His Lys Val Tyr Ala Cys Glu Val Thr His Gln Gly Leu Ser
                215                 220                 225

Ser Pro Val Thr Lys Ser Phe Asn Arg Gly Glu Cys
                230                 235


<210> SEQ ID NO 3
<211> LENGTH: 300
<212> TYPE: PRT
<213> ORGANISM: Human

<400> SEQUENCE: 3

Met Lys Lys Asn Ile Ala Phe Leu Leu Ala Ser Met Phe Val Phe
  1               5                  10                  15

Ser Ile Ala Thr Asn Ala Tyr Ala Glu Val Gln Leu Val Glu Ser
                 20                  25                  30

Gly Gly Gly Leu Val Gln Pro Gly Gly Ser Leu Arg Leu Ser Cys
                 35                  40                  45

Ala Thr Ser Gly Tyr Thr Phe Thr Glu Tyr Thr Met His Trp Met
                 50                  55                  60

Arg Gln Ala Pro Gly Lys Gly Leu Glu Trp Val Ala Gly Ile Asn
                 65                  70                  75

Pro Lys Asn Gly Gly Thr Ser His Asn Gln Arg Phe Met Asp Arg
                 80                  85                  90

Phe Thr Ile Ser Val Asp Lys Ser Thr Ser Thr Ala Tyr Met Gln
                 95                 100                 105

Met Asn Ser Leu Arg Ala Glu Asp Thr Ala Val Tyr Tyr Cys Ala
                110                 115                 120

Arg Trp Arg Gly Leu Asn Tyr Gly Phe Asp Val Arg Tyr Phe Asp
                125                 130                 135

Val Trp Gly Gln Gly Thr Leu Val Thr Val Ser Ser Ala Ser Thr
                140                 145                 150

Lys Gly Pro Ser Val Phe Pro Leu Ala Pro Ser Ser Lys Ser Thr
                155                 160                 165

Ser Gly Gly Thr Ala Ala Leu Gly Cys Leu Val Lys Asp Tyr Phe
                170                 175                 180

Pro Glu Pro Val Thr Val Ser Trp Asn Ser Gly Ala Leu Thr Ser
                185                 190                 195

Gly Val His Thr Phe Pro Ala Val Leu Gln Ser Ser Gly Leu Tyr
                200                 205                 210
```

-continued

```
Ser Leu Ser Ser Val Val Thr Val Pro Ser Ser Ser Leu Gly Thr
                215                 220                 225

Gln Thr Tyr Ile Cys Asn Val Asn His Lys Pro Ser Asn Thr Lys
                230                 235                 240

Val Asp Lys Lys Val Glu Pro Lys Ser Cys Asp Lys Thr His Thr
                245                 250                 255

Cys Pro Pro Cys Pro Ala Pro Glu Leu Leu Gly Gly Arg Met Lys
                260                 265                 270

Gln Leu Glu Asp Lys Val Glu Glu Leu Leu Ser Lys Asn Tyr His
                275                 280                 285

Leu Glu Asn Glu Val Ala Arg Leu Lys Lys Leu Val Gly Glu Arg
                290                 295                 300


<210> SEQ ID NO 4
<211> LENGTH: 11
<212> TYPE: PRT
<213> ORGANISM: Artificial
<220> FEATURE:
<221> NAME/KEY: Artificial
<222> LOCATION: 1-11
<223> OTHER INFORMATION: Hinge sequence

<400> SEQUENCE: 4

Cys Pro Pro Cys Pro Ala Pro Leu Leu Gly Gly
  1               5                  10
```